(12) United States Patent
Schoenfisch et al.

(10) Patent No.: US 8,551,322 B2
(45) Date of Patent: Oct. 8, 2013

(54) NITRIC OXIDE MICROSENSORS VIA FLUOROSILANE-BASED XEROGEL MEMBRANES

(75) Inventors: Mark H. Schoenfisch, Chapel Hill, NC (US); Jae Ho Shin, Chapel Hill, NC (US)

(73) Assignee: University of North Carolina at Chapel Hill

( * ) Notice: Subject to any disclaimer, the term of this patent is extended or adjusted under 35 U.S.C. 154(b) by 928 days.

(21) Appl. No.: 12/374,932

(22) PCT Filed: Aug. 24, 2007

(86) PCT No.: PCT/US2007/018718
§ 371 (c)(1),
(2), (4) Date: Nov. 12, 2009

(87) PCT Pub. No.: WO2008/073167
PCT Pub. Date: Jun. 19, 2008

(65) Prior Publication Data
US 2010/0051480 A1 Mar. 4, 2010

Related U.S. Application Data

(60) Provisional application No. 60/839,870, filed on Aug. 24, 2006.

(51) Int. Cl.
*G01N 27/26* (2006.01)
*G01F 1/64* (2006.01)
*B05D 5/12* (2006.01)
*C08G 77/24* (2006.01)

(52) U.S. Cl.
USPC ............ 205/781; 528/42; 205/792; 205/793; 204/415; 204/403.01; 600/364; 428/447; 427/387

(58) Field of Classification Search
USPC .............. 204/421–429, 403.01–403.15, 415; 205/775, 777.5, 792, 778, 781, 793; 528/42; 600/364; 428/447; 427/387
See application file for complete search history.

(56) References Cited

U.S. PATENT DOCUMENTS

| | | | |
|---|---|---|---|
| 4,614,575 A * | 9/1986 | Juda et al. ................. | 204/265 |
| 4,900,405 A | 2/1990 | Otagawa et al. | |
| 5,964,794 A | 10/1999 | Bolz et al. | |
| 6,165,336 A | 12/2000 | Maki et al. | |
| 6,383,642 B1 | 5/2002 | Le Bellac et al. | |
| 6,511,753 B1 * | 1/2003 | Teranishi et al. ............ | 428/447 |
| 6,589,644 B1 | 7/2003 | Yamada et al. | |

(Continued)

OTHER PUBLICATIONS

Sugimura et al. (Surfaces and Interface Analysis, 2002, 34, 550-554).*

(Continued)

*Primary Examiner* — J. Christopher Ball
*Assistant Examiner* — Jennifer Dieterle

(57) ABSTRACT

The presently disclosed subject matter relates to sensors for measuring an amount of a gaseous species in a sample. The sensors comprise a gas permeable polysiloxane network membrane, comprising both alkyl and fluorinated alkyl groups. In some embodiments, the polysiloxane network can be formed from the co-condensation of a mixture of an alkylalkoxysilane and a fluorosilane. The presently disclosed subject matter also relates to methods of making the sensors, methods of selectively measuring an amount of a gaseous species, such as nitric oxide, in a sample, and to compositions comprising the polysiloxane networks.

48 Claims, 14 Drawing Sheets

(56) References Cited

U.S. PATENT DOCUMENTS

| | | | |
|---|---|---|---|
| 7,918,978 B2 * | 4/2011 | McCann et al. | 204/435 |
| 2002/0001744 A1 | 1/2002 | Tsusaka et al. | |
| 2002/0011408 A1 | 1/2002 | Lee et al. | |
| 2002/0070112 A1 * | 6/2002 | Lee et al. | 204/431 |
| 2004/0211242 A1 | 10/2004 | Holmuhamedov | |

OTHER PUBLICATIONS

Iwata et al. (Journal of Applied Polymer Science, vol. 88, 1752-1759, 2003.*

* cited by examiner

NITRIC OXIDE MICROSENSORS VIA FLUOROSILANE-BASED XEROGEL MEMBRANES

RELATED APPLICATIONS

This application claims the benefit of U.S. Provisional Patent Application Ser. No. 60/839,870, filed Aug. 24, 2006; the disclosure of which is incorporated herein by reference in its entirety.

GOVERNMENT INTEREST

This invention was made with U.S. Government support from National Institutes of Health Grant Number EB000708. Thus, the U.S. Government has certain rights in the invention.

TECHNICAL FIELD

The presently disclosed subject matter relates to sensors comprising a gas permeable membrane comprising alkyl and fluorinated alkyl groups. The sensors can be used as biosensors for the detection and measurement of biologically relevant gaseous species, including nitric oxide and oxygen. Also provided are methods for making the sensors, methods of measuring an amount of a gaseous species in a sample, and compositions comprising polysiloxane networks having alkyl and fluorinated alkyl substituents.

ABBREVIATIONS atm=atmosphere
BTMOS=butyltrimethoxysilane
° C.=degrees Celsius
EtOH=ethanol
g=grams
h=hours
HTMOS=hexyltrimethoxysilane
MeOH=methanol
mg=milligrams
min=minutes
μL=microliters
mL=milliliters
μm=micrometers
μM=micromolar
mm=millimeters
MRI=magnetic resonance imaging
MTMOS=methyltrimethoxysilane
nA=nanoampere
nm=nanometers
nM=nanomolar
NMR=nuclear magnetic resonance
NO=nitric oxide
$NO_2^-$=nitrite
NOS=nitric oxide synthase
OTMOS=octyltrimethoxysilane
pA=picoampere
pM=picomolar
PBS=phosphate-buffered saline
Pt=platinum

BACKGROUND

Nitric oxide (NO) is a diatomic free radical endogenously synthesized in the human body when L-arginine is converted to L-citrulline by a class of enzymes known as nitric oxide synthases (NOS's). Since the first reports describing NO's action as an endothelium-derived relaxation factor, much research has been devoted to elucidating the pathways of NO generation and action in biological milieu. In particular, NO is involved in neurotransmission, vasodilation, immune responses (including anti-tumor and anti-microbial activities), the inhibition of platelet aggregation, and in blood pressure control. See Zhang, X., *Frontiers in Bioscience*, 9, 3434-3446 (2004).

Miniaturized electrochemical sensors represent promising devices for determining the spatial and temporal distributions of NO in physiology. The use of such sensors, however, has been limited by low sensitivity, comparatively slow response time, and/or interferences from other readily oxidizable biological species (e.g., nitrite, ascorbic acid, uric acid, and dopamine).

In attempts to address these limitations, a variety of permselective polymers have been synthesized and employed as sensor membranes. For example, poly(tetrafluoroethylene) (TEFLON®, E. I. du Pont de Nemours and Company, Wilmington, Del., United States of America) has proven to be a selective membrane resulting in the fabrication of nitric oxide sensors with good sensitivity. Unfortunately, the poor solubility of poly(tetrafluoroethylene) in standard organic solvents and the intricate process required to mount or coat such films onto electrodes has hindered its utility as a membrane for fabricating microsensors, including those for use in detecting and measuring nitric oxide.

Accordingly, there is a need in the art for gas permeable materials for use as sensor membranes. In particular, there is a need for gas permeable materials that can be synthesized using common solvents and via methods that can be readily modified to tailor the permeability and selectivity of the materials for a specific use and to easily coat a variety of sensor shapes and materials.

SUMMARY

In some embodiments, the presently disclosed subject matter provides a sensor for measuring an amount of a gaseous species in a sample, the sensor comprising:
  (a) an electrode assembly;
  (b) a gas permeable membrane located between one or more surfaces of the electrode assembly and the sample, wherein the membrane comprises a polysiloxane network wherein one or more silicon atoms in the polysiloxane network is covalently attached to an alkyl group and one or more silicon atoms in the polysiloxane network is covalently attached to a fluorinated alkyl group; and
  (c) a detector for measuring current at the electrode assembly.

In some embodiments, the gaseous species is selected from nitric oxide and oxygen.

In some embodiments, the electrode assembly is selected from the group consisting of:
  an electrode assembly comprising a working electrode;
  an electrode assembly comprising a working electrode and a reference electrode; and
  an electrode assembly comprising a working electrode, a reference electrode, and a counter electrode.

In some embodiments, the working electrode comprises a material selected from platinum, platinized platinum, tungsten, gold, carbon, carbon fiber, and combinations thereof. In some embodiments, the reference electrode comprises silver/silver chloride. In some embodiments, the counter electrode comprises platinum.

In some embodiments, the polysiloxane network is a condensation product of a silane mixture comprising an alkylalkoxysilane and a fluorosilane.

In some embodiments, the fluorosilane comprises a structure having a formula:

$$F_3C-(CF_2)_m-(CH_2)_n-Si(X)_p(Y)_{3-p}$$

wherein:
m is 0 to 15;
n is 1 to 5;
p is 1, 2, or 3;
each X is independently selected from the group consisting of alkoxy, aryloxy, aralkoxy, hydroxyl, and halo; and
each Y is independently selected from the group consisting of H, alkyl, aryl, and aralkyl.

In some embodiments, the fluorosilane is selected from the group consisting of:
(3,3,3-trifluoropropyl)trimethoxysilane;
nonafluorohexyltrimethyoxysilane;
nonafluorohexyltriethoxysilane;
(tridecafluoro-1,1,2,2-tetrahydrooctyl)trimethoxysilane;
(tridecafluoro-1,1,2,2-tetrahydrooctyl)triethoxysilane;
(tridecafluoro-1,1,2,2-tetrahydrooctyl)trichlorosilane;
(heptadecafluoro-1,1,2,2-tetrahydrodecyl)trimethoxysilane;
(heptadecafluoro-1,1,2,2-tetrahydrodecyl)triethoxysilane;
(perfluoroalkyl)ethyltriethoxysilane;
(heptadecafluoro-1,1,2,2-tetrahydrodecyl)trichlorosilane; and
combinations thereof.

In some embodiments, the alkylalkoxysilane is selected from the group consisting of:
methyltrimethoxysilane (MTMOS);
ethyltrimethoxysilane;
propyltrimethoxysilane;
butyltrimethoxysilane (BTMOS);
hexyltrimethoxysilane (HTMOS);
octyltrimethoxysilane (OTMOS); and
combinations thereof.

In some embodiments, the silane mixture comprises about 1% to about 99% by volume fluorosilane. In some embodiments, the silane mixture comprises about 5% to about 50% by volume fluorosilane. In some embodiments, the silane mixture comprises about 20% by volume fluorosilane.

In some embodiments, the silane mixture comprises about 20% by volume (heptadecafluoro-1,1,2,2-tetrahydrodecyl)triethoxysilane and about 80% by volume methyltrimethoxysilane.

In some embodiments, the sensor comprises an internal electrolyte layer, wherein the internal electrolyte layer is located between the electrode assembly and the gas permeable membrane. In some embodiments, the internal electrolyte layer is a hydrogel composition. In some embodiments, the hydrogel composition comprises poly(vinylpyrrolidone).

In some embodiments, the presently disclosed subject matter provides a method of making a sensor for measuring an amount of a gaseous species in a sample, the method comprising:
(a) providing a silane mixture comprising a fluorosilane and an alkylalkoxysilane;
(b) providing an electrode assembly;
(c) coating at least one portion of the electrode assembly with the silane mixture to form a coated electrode; and
(d) drying the coated electrode to form a gas permeable polysiloxane membrane layer on at least one portion of the electrode assembly.

In some embodiments, the silane mixture is dissolved in a solvent. In some embodiments, the solvent comprises an alcohol and water. In some embodiments, the alcohol is ethanol.

In some embodiments, the solvent comprises a catalyst. In some embodiments, the catalyst is hydrochloric acid.

In some embodiments, the drying takes place at ambient temperature. In some embodiments, the drying takes place at an elevated temperature. In some embodiments, the drying step further comprises exposing the membrane layer to one of nitric oxide or argon at a pressure.

In some embodiments, the coating is performed by dipping the electrode assembly into the silane mixture.

In some embodiments, the method further comprises repeating the coating and drying steps one or more times to provide a thicker membrane layer.

In some embodiments, prior to coating the at least one portion of the electrode assembly with the silane mixture, the at least one portion of the electrode assembly is coated with a hydrogel material.

In some embodiments, the presently disclosed subject matter provides a sensor prepared by a method comprising:
(a) providing a silane mixture comprising a fluorosilane and an alkylalkoxysilane;
(b) providing an electrode assembly;
(c) coating at least one portion of the electrode assembly with the silane mixture to form a coated electrode; and
(d) drying the coated electrode to form a gas permeable polysiloxane membrane layer on at least one portion of the electrode assembly.

In some embodiments, the presently disclosed subject matter provides a method of measuring an amount of a gaseous species in a sample, the method comprising contacting the sample with a sensor comprising a polysiloxane membrane, wherein the polysiloxane membrane comprises one or more silicon atoms covalently attached to an alkyl group and one or more silicon atoms covalently attached to a fluorinated alkyl group, and further wherein the polysiloxane membrane selectively allows the gaseous species in the sample to be measured by the sensor.

In some embodiments, the sensor is an amperometric sensor.

In some embodiments, the polysiloxane membrane is positioned between the sample and an electrode assembly.

In some embodiments, the sample is a biological sample or an environmental sample. In some embodiments, the biological sample is selected from a cell, a tissue, a biological fluid, or an extract thereof. In some embodiments, the sample comprises brain cells, macrophages, neutrophils, or blood. In some embodiments, the sample is in a living subject. In some embodiments, the sample is in the brain of a living subject. In some embodiments, the sample comprises a single cell.

In some embodiments, the gaseous species is nitric oxide or oxygen. In some embodiments, the gaseous species is measured at a concentration as low as 200 pM.

In some embodiments, the presently disclosed subject matter provides a composition comprising a polysiloxane network, wherein one or more silicon atom in the polysiloxane network is covalently attached to an alkyl group and one or more silicon atom in the polysiloxane network is covalently attached to a fluorinated alkyl group having a structure of:

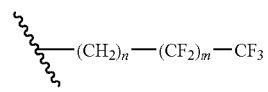

wherein m is 0 to 15 and n is 1 to 5.

In some embodiments, each silicon atom in the polysiloxane network is covalently attached to an alkyl group or to a fluorinated alkyl group.

In some embodiments, the polysiloxane network is selectively permeable to a biologically relevant gaseous species. In some embodiments, the biologically relevant gaseous species is selected from the group consisting of nitric oxide and oxygen.

In some embodiments, the polysiloxane network is a condensation product of a silane mixture comprising an alkylalkoxysilane and a fluorosilane. In some embodiments, the polysiloxane network is formed by a sol-gel process.

Thus, it is an object of the presently disclosed subject matter to provide sensors, compositions, and methods related to measuring an amount of a gaseous species in a sample.

An object of the presently disclosed subject matter having been stated herein above, which are addressed in whole or in part by the presently disclosed subject matter, other objects and aspects will become evident as the description proceeds when taken in connection with the accompanying Examples as best described herein below.

DETAILED DESCRIPTION

Figure 1:
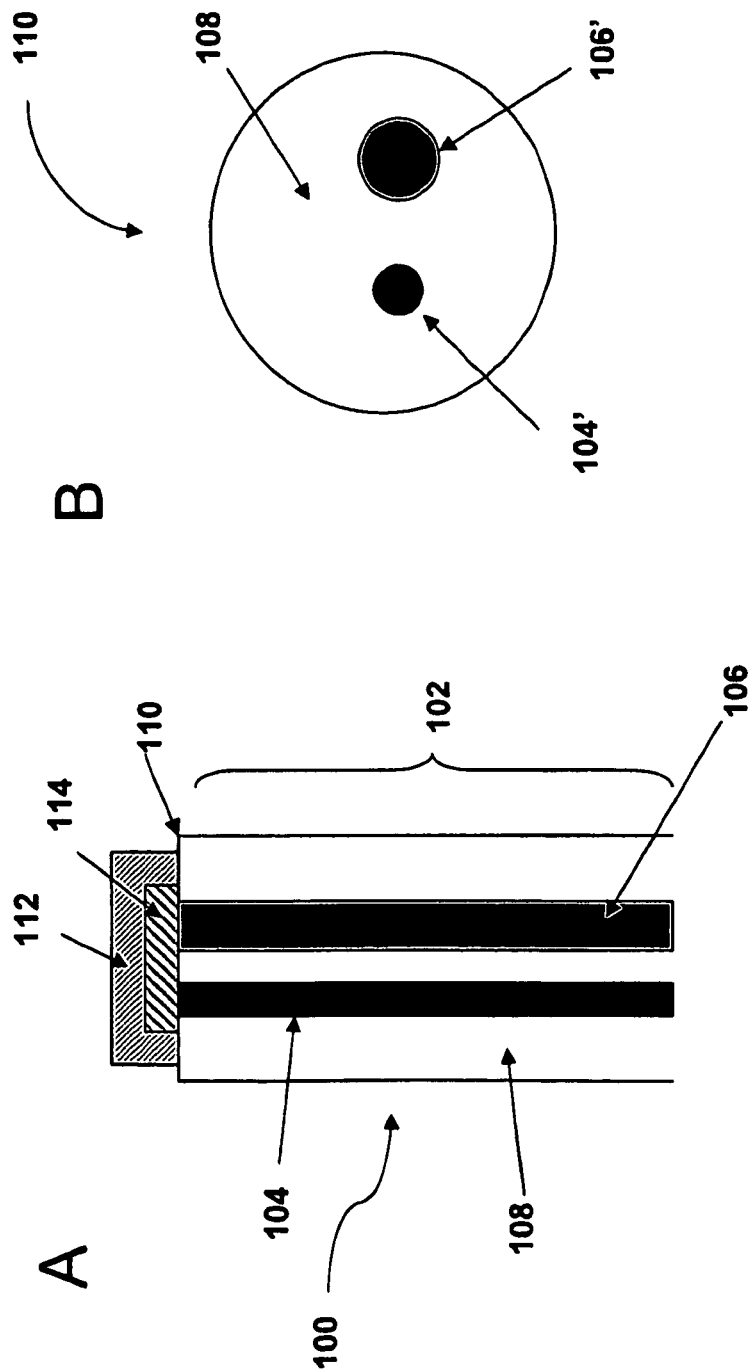
FIG. 1A is a schematic illustration of a longitudinal cross view of an electrode assembly comprising a xerogel membrane-coated sensing tip.
FIG. 1B is a schematic illustration of a top view of the sensing end of the electrode described in FIG. 1A, shown in the absence of any electrode assembly tip coatings.

The presently disclosed subject matter will now be described more fully hereinafter with reference to the accompanying Examples, in which representative embodiments are shown. The presently disclosed subject matter can, however, be embodied in different forms and should not be construed as limited to the embodiments set forth herein. Rather, these embodiments are provided so that this disclosure will be thorough and complete, and will fully convey the scope of the embodiments to those skilled in the art.

Unless otherwise defined, all technical and scientific terms used herein have the same meaning as commonly understood by one of ordinary skill in the art to which this presently described subject matter belongs. All publications, patent applications, patents, and other references mentioned herein are incorporated by reference in their entirety.

Throughout the specification and claims, a given chemical formula or name shall encompass all optical and stereoisomers, as well as racemic mixtures where such isomers and mixtures exist.

I. DEFINITIONS

Following long-standing patent law convention, the terms "a" and "an" mean "one or more" when used in this application, including the claims.

The term "about," as used herein, when referring to a value or to an amount of mass, weight, time, volume, diameter, or percentage is meant to encompass variations of ±20% or ±10%, more preferably ±5%, even more preferably ±1%, and still more preferably ±0.1% from the specified amount, as such variations are appropriate to perform the disclosed method.

The term "hydrophobic" refers to a chemical compound or moiety that, to a given extent, repels or does not interact with water through non-covalent forces such as hydrogen bonding or electrostatic interactions. A compound can be strongly hydrophobic or slightly hydrophobic. The calculated dielectric constant of a compound or group can be used to predict the level or degree of hydrophobicity of the compound or moiety. Compounds or moieties with lower dielectric constants will be more hydrophobic.

The term "porous" refers to a material having pores. The material can be mesoporous, comprising pores in the range of between about 20-500 angstroms. The material can be macroporous and comprise pores having a diameter greater than about 50 nm.

As used herein the term "alkyl" refers to $C_1$-$C_{20}$ inclusive, linear (i.e., "straight-chain"), branched, or cyclic, saturated or at least partially and in some cases fully unsaturated (i.e., alkenyl and alkynyl)hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups. "Branched" refers to an alkyl group in which a lower alkyl group, such as methyl, ethyl or propyl, is attached to a linear alkyl chain. Exemplary branched alkyl groups include, but are not limited to, isopropyl, isobutyl, tert-butyl, "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto. In some embodiments, the substituted alkyl group is a fluorinated alkyl group.

The term "fluorinated alkyl" refers to an alkyl group (i.e., $C_1$-$C_{20}$ linear, branched, or cyclic alkyl) wherein one or more of the C—H bonds are replaced by C—F bonds. In some embodiments, the entire length or a portion of the entire length (i.e., several consecutive carbon atoms) of the alkyl group is perfluorinated (i.e., each of the C—H bonds is replaced by a C—F bond).

The term "aryl" is used herein to refer to an aromatic substituent that can be a single aromatic ring, or multiple aromatic rings that are fused together, linked covalently, or linked to a common group, such as, but not limited to, a methylene or ethylene moiety. The common linking group also can be a carbonyl, as in benzophenone, or oxygen, as in diphenylether, or nitrogen, as in diphenylamine. The term "aryl" specifically encompasses heterocyclic aromatic compounds. The aromatic ring(s) can comprise phenyl, naphthyl, biphenyl, diphenylether, diphenylamine and benzophenone, among others. In particular embodiments, the term "aryl" means a cyclic aromatic comprising about 5 to about 10 carbon atoms, e.g., 5, 6, 7, 8, 9, or 10 carbon atoms, and including 5 and 6-membered hydrocarbon and heterocyclic aromatic rings.

The aryl group can be optionally substituted (a "substituted aryl") with one or more aryl group substituents, which can be the same or different, wherein "aryl group substituent" includes alkyl, substituted alkyl, aryl, substituted aryl, aralkyl, hydroxyl, alkoxyl, aryloxyl, aralkyloxyl, carboxyl, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene, and —NR'R", wherein R' and R" can each be independently hydrogen, alkyl, substituted alkyl, aryl, substituted aryl, and aralkyl.

Thus, as used herein, the term "substituted aryl" includes aryl groups, as defined herein, in which one or more atoms or functional groups of the aryl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

Specific examples of aryl groups include, but are not limited to, cyclopentadienyl, phenyl, furan, thiophene, pyrrole, pyran, pyridine, imidazole, benzimidazole, isothiazole, isoxazole, pyrazole, pyrazine, triazine, pyrimidine, quinoline, isoquinoline, indole, carbazole, fluorene, and the like.

"Aralkyl" refers to an aryl-alkyl- group wherein aryl and alkyl are as previously described, and included substituted aryl and substituted alkyl. Exemplary aralkyl groups include benzyl, phenylethyl, and naphthylmethyl.

"Alkoxyl" refers to an alkyl-O— group wherein alkyl is as previously described. The term "alkoxyl" as used herein can refer to, for example, methoxyl, ethoxyl, propoxyl, isopropoxyl, butoxyl, t-butoxyl, and pentoxyl. The terms "oxyalkyl" and "alkoxy" can be used interchangeably with "alkoxyl".

"Aryloxyl" and "aryloxy" refer to an aryl-O— group wherein the aryl group is as previously described, including a substituted aryl. The term "aryloxyl" as used herein can refer to phenyloxyl or hexyloxyl, and alkyl, substituted alkyl, halo, or alkoxyl substituted phenyloxyl or hexyloxyl.

"Aralkyloxyl," "aralkoxy," and "aralkyloxy" refer to an aralkyl-O— group wherein the aralkyl group is as previously described. An exemplary aralkyloxyl group is benzyloxyl.

The terms "halo", "halide", or "halogen" as used herein refer to fluoro, chloro, bromo, and iodo groups.

The term "hydroxyl" and "hydroxy" refer to the —OH group.

The term "hydroxyalkyl" refers to an alkyl group substituted with an —OH group.

The terms "silyl" and "silane" refer to chemical groups and compounds comprising silicon atoms (Si).

As used herein the term "alkoxysilane" refers to a compound comprising one, two, three, or four alkoxy groups bonded to a silicon atom. For example, tetraalkoxysilane refers to $Si(OR)_4$, wherein R is alkyl. Each alkyl group can be the same or different.

An "alkylalkoxysilane" refers to an alkoxysilane wherein one, two or three of the alkoxy groups has been replaced with an alkyl group (i.e., a $R'—Si(OR)_3$ group, a $R'_2—Si(OR)_2$ group or a $R'_3—Si(OR)$ group). Each alkyl group can be the same or different. Thus, an alkylalkoxysilane comprises at least one carbon-Si bond.

The term "fluorosilane" refers to a silane comprising one or more fluorine atoms. In some embodiments, the fluorosilane is a compound comprising a silicon atom attached to at least one fluorinated alkyl group. In some embodiments, the fluorosilane comprises a compound of the formula $R''Si(X)_p(Y)_{3-p}$, wherein p is an integer from 1-3; R" is a fluorinated alkyl group, each X is a hydrolyzable group (e.g., alkoxy, aryloxy, aralkoxy, hydroxyl or halo), and each Y is H, alkyl, aryl, or aralkyl. In some embodiments, p is 3 and the fluorosilane comprises a compound of the formula $R''Si(X)_3$. In some embodiments, each X group is selected from alkoxy, hydroxyl, and halo. In some embodiments, each X is ethoxy, methoxy or chloro.

The term "silanol" refers to the —Si—OH group.

The term "polysiloxane" refers to a polymeric material comprising a backbone of silicon-oxygen bonds (i.e., —Si—O—Si—O—Si—) having the formula $R_nSiX_yO_m$, wherein each R is an H, alkyl, aryl, aralkyl, or substituted alkyl group and each X is an alkoxy, aryloxy, aralkoxy, hydroxyl or halo group. In some embodiments, each silicon atom is covalently bonded to one R group, for example one alkyl or fluorinated alkyl group. Each silicon atom is also crosslinked to one, two, or three other silicon atoms via silicon-oxygen bonds and bonded to zero, one, or two X groups, such as ethoxy, methoxy, hydroxyl, or chloro. Thus, in some embodiments, higher the level of crosslinking in the polysiloxane, the fewer X groups are present. The terms "polysiloxane" and "silicone" can be used interchangeably.

As used herein, the term "oxygen" when referring to a gas, refers to dioxygen, i.e., $O_2$.

The term "co-condensation" and "co-condensed" refer to materials that are formed when two different compounds (such as, for example, a fluorosilane and an alkylalkoxysilane) react with each other to form a third compound and to give off a molecule or molecules of an alcohol or water.

The term "xerogel" as used herein refers to a polymeric network formed via a sol-gel process. In particular, the term xerogel can be used to refer to polysiloxane networks formed from the co-condensation of solutions containing silane mixtures.

The term "permselective" refers to selective permeability, for example, of a material, such as a membrane. Thus, a permselective or selectively permeable membrane allows some molecules to pass through the membrane, while other molecules cannot pass through the membrane. In some embodiments, the term "permselective" as used herein refers to a membrane that selectively allows small, nonpolar gaseous molecules to pass through, while being impermeable to larger or more polar molecules.

Thus, in some embodiments, the permselective or selectively permeable material or membrane is selectively permeable to nitric oxide and oxygen, while not being permeable to compounds such as nitrite ($NO_2^-$), ascorbic acid, uric acid, acetaminophen, dopamine, and aqueous liquids.

II. POLYSILOXANE COMPOSITIONS

In some embodiments, the presently disclosed subject matter provides a polysiloxane network comprising at least one silicon atom having an alkyl group substituent and at least one silicon atom having a fluorinated alkyl group substituent, wherein the fluorinated alkyl group has the structure:

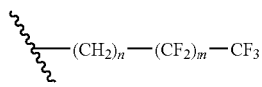

wherein m is 0 to 15 and n is 1 to 5. In some embodiments, each of the silicon atoms in the polysiloxane network is covalently attached to either an alkyl group or to a fluorinated alkyl group.

In some embodiments, the polysiloxane network is selectively permeable to a biologically relevant gaseous species, for example, to nitric oxide and/or oxygen ($O_2$).

In some embodiments, the polysiloxane network is a co-condensed product of a silane mixture comprising an alkylalkoxysilane and a fluorosilane.

In some embodiments, the fluorosilane comprises a structure having a formula:

wherein:
  m is 0 to 15;
  n is 1 to 5;
  p is 1, 2, or 3;
  each X is independently selected from the group consisting of alkoxy, aryloxy, aralkoxy, hydroxyl, and halo; and
  each Y is independently selected from the group consisting of H, alkyl, aryl, and aralkyl.

Thus, the fluorosilane can comprise a fluorinated alkyl group and at least one hydrolyzable group that can take place in a condensation reaction. The silicon atom of the fluorosilane can also be attached to one or two non-fluorinated, non-hydrolyzable groups. In some embodiments, p is 2 and the fluorosilane can comprise two X groups and one Y group. In some embodiments, p is 1 and the fluorosilane can comprise one X group and two Y groups.

In some embodiments, each of the silicon atom substituents of the fluorosilane is either a fluorinated alkyl group or a hydrolyzable group. Thus, in some embodiments, p is 3, and the fluorosilane can have the formula:

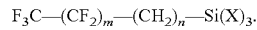

In some embodiments, each X is independently alkoxy or halo. For in example, each X can be ethoxy, methoxy, or chloro. In some embodiments, each Y is alkyl.

In some embodiments, the fluorosilane is selected from the group consisting of:
  (3,3,3-trifluoropropyl)trimethoxysilane;
  nonafluorohexyltrimethyoxysilane;
  nonafluorohexyltriethoxysilane;

(tridecafluoro-1,1,2,2-tetrahydrooctyl)trimethoxysilane;
(tridecafluoro-1,1,2,2-tetrahydrooctyl)triethoxysilane;
(tridecafluoro-1,1,2,2-tetrahydrooctyl)trichlorosilane;
(heptadecafluoro-1,1,2,2-tetrahydrodecyl)trimethoxysilane;
(heptadecafluoro-1,1,2,2-tetrahydrodecyl)triethoxysilane;
(perfluoroalkyl)ethyltriethoxysilane;
(heptadecafluoro-1,1,2,2-tetrahydrodecyl)trichlorosilane; and
combinations thereof.

In some embodiments, the alkylalkoxysilane is selected from the group consisting of: methyltrimethoxysilane (MTMOS); ethyltrimethoxysilane; propyltrimethoxysilane; butyltrimethoxysilane (BTMOS); hexyltrimethoxysilane (HTMOS); octyltrimethoxysilane (OTMOS); and combinations thereof.

In some embodiments, the silane mixture comprises about 1% to about 99% by volume fluorosilane. In some embodiments, the silane mixture comprises about 5% to about 50% by volume fluorosilane. In some embodiments, the silane mixture comprises about 20% by volume fluorosilane. In some embodiments, the silane mixture comprises about 20% by volume (heptadecafluoro-1,1,2,2-tetrahydrodecyl)triethoxysilane and about 80% by volume methyltrimethoxysilane.

In some embodiments, the polysiloxane network is a xerogel formed using a sol-gel polymerization process. In a sol-gel process, precursors of the polysiloxane network (e.g., the alkylalkoxysilane and the fluorosilane) are present in a solution. For example, the precursors can be dissolved in a solvent. The solvent can comprise water and an alcohol, such as, ethanol, methanol, propanol, and the like. As polymerization proceeds, the precursors bond to one another, forming a macromolecule (i.e., a gel).

The "sol-gel" process of forming the polysiloxane network can involve two types of chemical reactions. The first step involves a hydrolysis reaction in which an alkoxy or chloro group of an alkylalkoxysilane and/or a fluorosilane is hydrolyzed, thereby forming a silanol group (i.e., a hydroxy group attached to the Si atom). The hydrolysis reaction can be catalyzed by Bronstead acids or bases (i.e., groups that generate $H^+$ or $OH^-$ ions), such as, for example, acetic acid or hydrochloric acid. The second step is a condensation reaction wherein two silanols or a silanol and an alkoxysilane react to form a siloxane bond (i.e., Si—O—Si) while releasing a molecule of water or a molecule of an alcohol.

The presently disclosed fluorosilane-based materials can be analyzed using solid state $^{29}Si$ NMR, using surface wettability measurements, and using electrochemical techniques to monitor changes in the chemical structure of the xerogel as a function of precursor composition and processing conditions.

For example, the level of co-condensation in the polymeric silane-based network can be monitored using solid state $^{29}Si$ NMR by assessing changes in relative amounts of NMR peaks associated with three different types of silyl group, which are illustrated below in Scheme 1. One type of silyl group comprises two hydroxyl groups (structure A in Scheme 1), one R group (i.e., an alkyl or fluorinated alkyl group) and is attached to the co-condensed silicone network via one siloxane bond (as indicated by the wavy line). A second type of silyl group comprises one hydroxyl group, one R group, and has two attachment sites to the network (structure B). A third type of silyl group (structure C) comprises three attachment sites to the network and one R group.

Scheme 1. Silyl Group Structures.

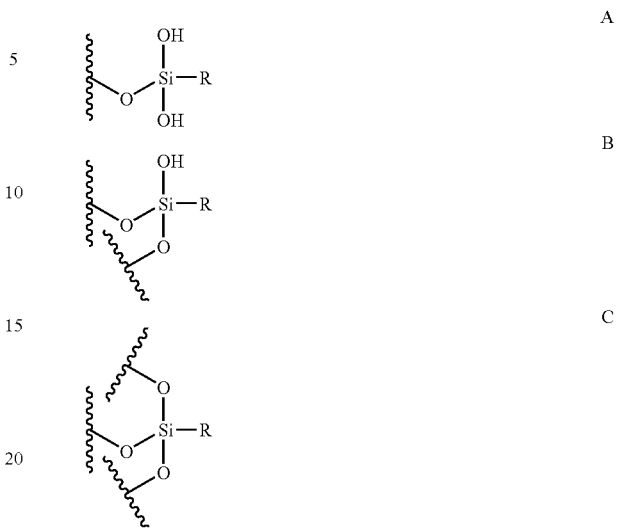

Xerogel stability to various potential use conditions can also be tested. For instance, a xerogel membrane can be soaked in a solution at a given pH or temperature for a period of time, and the Si concentration in the solution can be measured (e.g. using direct current plasma optical emission spectroscopy) to determine the amount of membrane fragmentation. The xerogels can also be tested to determine their permselectivity to particular gaseous or non-gaseous species of interest. In certain embodiments, it can be desirable to determine the biocompatibility of the presently disclosed fluorosilane-based xerogel membranes, depending upon the desired end use of the membranes or the devices prepared with the membranes. Thus, in some embodiments, the xerogel can be tested to determine its immunogenicity and/or its affinity for antibodies, proteins, and/or other biological components that can be present in mammalian cells, tissues or fluids.

For example, when the presently disclosed fluorosilane-based xerogel membranes are to be in contact with blood (e.g., in intravenous use), it can be desirable to assess and/or tailor the thromboresistivity of the membranes. In some embodiments, thromboresistivity can be assessed according to the membrane's ability to resist platelet adhesion using an in vitro platelet adhesion assay. Marxer, S. M., et al., Analyst, 130, 206-212 (2005). Factors that can change from xerogel to xerogel, such as wettability and surface roughness, are believed to be able to affect membrane thromboresistivity. See Marxer, S. M. et al., Analyst, 130, 206-212 (2005). Surface wettability of a membrane can be determined by measuring the water contact angles of a membrane, for instance, before and after exposure to water for one or more periods of time. Surface roughness can be assessed via microscopy, such as atomic force microscopy or any other suitable microscopy method. See Marxer, S. M., et al., Analyst, 130, 206-212 (2005).

III. SENSORS

The presently disclosed subject matter provides sensors comprising gas permeable membranes comprising polysiloxane networks. The polysiloxane networks comprise both alkyl and fluorinated alkyl groups.

Generally, the presently disclosed sensors can detect the presence of the gaseous species using an electrochemical technique, such as a voltammetric or coulometric technique. In some embodiments, the sensor is an amperometric sensor (i.e., it detects the redox current produced by the oxidation of the gaseous species over time at a fixed voltage potential). In some embodiments, the detector is a potentiostat.

Thus, in some embodiments, the presently disclosed subject matter provides a sensor for measuring an amount of a gaseous species in a sample, the sensor comprising:

(a) an electrode assembly;

(b) a gas permeable membrane located between one or more surfaces of the electrode assembly and the sample, wherein the membrane comprises a polysiloxane network wherein one or more silicon atoms in the polysiloxane network is covalently attached to an alkyl group and one or more silicon atoms in the polysiloxane network is covalently attached to a fluorinated alkyl group; and (c) a detector for measuring current at the electrode assembly.

In some embodiments, the gaseous species is selected from nitric oxide and oxygen. In some embodiments, the membrane is selectively permeable to one or more of nitric oxide and oxygen. Thus, in some embodiments, the presently disclosed sensors comprise membranes that are macro- or mesoporous, and allow some molecules to pass into or through the membrane. Other molecules cannot pass through the membrane because of their size or because of electrostatic repulsion with the membrane material. In particular, without being bound to any one particular theory, because the presently described polysiloxane network membranes are composed of silanes having non-hydrophilic substituents (i.e., alkyl or fluorinated alkyl groups), in some embodiments, the networks are selectively permeable to neutral molecules (e.g., NO and $O_2$) in comparison with charged species (e.g., nitrite ($NO_2^-$)).

The electrode assembly can comprise one, two, three, or more electrodes. In some embodiments, the electrode assembly comprises one electrode (i.e., a working electrode). In some embodiments, the sensor includes a two- or a three-electrode configuration. Thus, in some embodiments, the electrode assembly comprises a working electrode and a reference electrode. In some embodiments, the electrode assembly comprises a working electrode, a counter electrode, and a reference electrode.

The electrode assembly can further include one or more insulating materials or components to physically contain at least a portion of the electrode or electrodes, or to insulate electrodes from one another. In some embodiments, the electrode assembly can comprise a coating to protect the electrode or electrodes from the environment and/or to enhance the biocompatibility of the electrode assembly. For example, the electrode assembly can comprise a biocompatible polymeric coating covering those portions of the assembly not covered by the gas permeable membrane, so long as such coating does not interfere with the ability of the sensor to detect the gaseous species.

Suitable electrode materials include any electrically conductive metals and other materials such as, but not limited to, platinum, palladium, rhodium, ruthenium, osmium, iridium, tungsten, nickel, copper, gold, silver, and carbon and carbon fibers, as well as, oxides, dioxides, combinations, or alloys thereof. In some embodiments, the electrically conductive material is selected from carbon (including glassy carbon), carbon fibers, platinum (including platinized platinum), tungsten, silver, silver/silver chloride, gold, copper, indium tin oxide, iridium oxide, nickel and combinations thereof. In some embodiments, the working electrode comprises a material selected from platinum, platinized platinum, tungsten, gold, carbon, carbon fiber, and combinations thereof. In some embodiments, the reference electrode comprises silver/silver chloride. In some embodiments, the counter electrode comprises platinum.

The dimensions of the sensor can be varied to suit a particular use. The presently disclosed sensors include microsensors having a sensor tip (i.e., an area where the membrane-coated electrode assembly is exposed to the sample) with a diameter of between about 1 μm and about 1 mm. In some embodiments, the microsensor has a sensor tip diameter of 1 μm or less. Microsensors having a sensor tip diameter of about 10 μm can also be referred to as "ultramicrosensors." The presently disclosed sensors also include macrosensors, having a sensor tip diameter of about 1-10 mm.

The sensors can be flexible or rigid. In some embodiments, the sensors can include both rigid and flexible components. The inclusion of a flexible component can be based upon the desired end use of the sensor. For example, flexible components can be advantageous in the positioning, retrieval, and/or use of a sensor in vivo.

In some embodiments, the polysiloxane network is a condensation product of a silane mixture comprising an alkylalkoxysilane and a fluorosilane. The chemical structure and the relative amounts of the silanes in the silane mixture can be varied to alter the biocompatibility, surface wettability and porosity characteristics of the polysiloxane network, depending upon the intended use of the sensor.

In some embodiments, the sensor can further comprise an internal electrolyte layer located between the electrode assembly or a portion of the electrode assembly and the gas permeable membrane. In some embodiments, the internal electrolyte layer is a hydrogel composition. Suitable hydrogels include hydrogels used in medical electrodes, such as, but not limited to, hydrogel compositions comprising polyethylene glycol (PEG), polyacrylamides, poly(2-arylamido-2-methyl-1-propanesulfonic acid) (polyAMPS), and polyvinylpyrrolidone. In some embodiments, the hydrogel composition comprises polyvinylpyrrolidone.

In some embodiments, the sensor can be a Clark-type sensor, including a working electrode and a reference electrode, each electrode inserted into a separate barrel of a glass capillary tube. Suitable glass capillary tubes are available, for example, from World Precision Instruments, Sarasota, Fla., United States of America). At the end of the capillary tube, the ends of the electrodes are exposed from the glass and are covered by the gas permeable membrane.

FIG. 1A shows a schematic illustration of a longitudinal cross view of a representative Clark-type sensor 100, which comprises a coating of fluorosilane-based xerogel. The shaft of sensor 100 comprises electrode assembly 102, which includes both working electrode 104 and reference electrode 106. The electrodes can be of any suitable electrode material and can have any suitable dimensions to correspond to the desired dimensions of the electrode assembly and/or sensor as a whole. In some embodiments, the electrodes can have outer diameters ranging from between a few mm and a few tenths of a micrometer. Working electrode 104 can comprise, for example, platinized Pt having an outer diameter of 127 μm. Reference electrode 106 can comprise Ag/AgCl, having an outer diameter of 250 μm. Thus, electrode assembly 102 can have an outer diameter of, for example, 1.5 mm. Electrodes 104 and 106 are surrounded by insulating material 108 (e.g., borosilicate glass), which insulates electrodes 104 and 106 from one another. End 110 of electrode assembly 102 is covered by a layer of fluorosilane-based xerogel 112. Thus, to reach electrodes 104 and 106, any species from a sample that comes into contact with sensor 100 must first diffuse through xerogel 112. The other end of electrode assembly 102 (not shown) can be attached to the detector. Sandwiched between electrodes 104 and 106 and xerogel 112 is hydrogel 114, which is optional.

FIG. 1B is a schematic illustration showing the view looking down on on electrode assembly 102 at the surface of electrode assembly end 110. End 104' of working electrode 104 and end 106' of working electrode 106 are not covered by insulating material 108 at the surface of end 110.

Figure 2A:
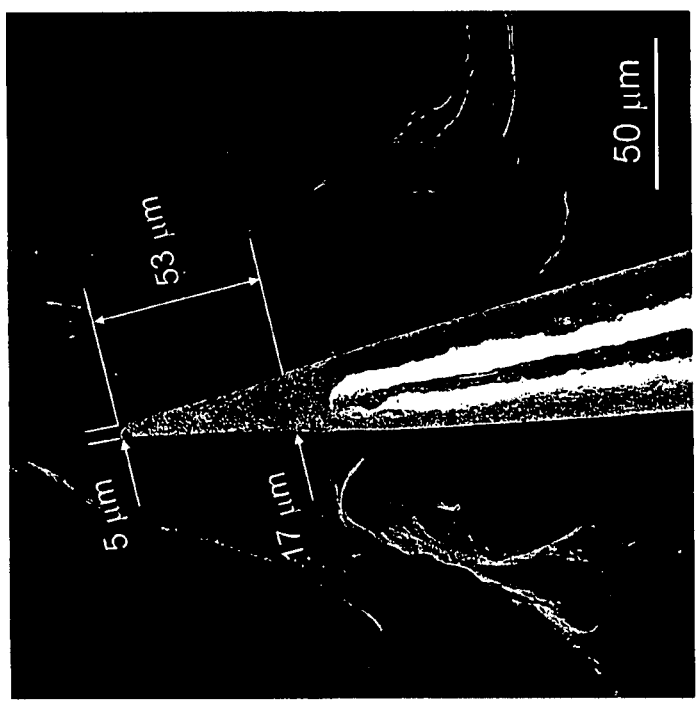
FIG. 2A is a scanning electron micrograph of a platinized tungsten-platinum wire microelectrode. An approximately 53 µm long section of the tapered end portion of the microelectrode is coated by platinum black. The tip of the microelectrode has a diameter of 5 µm. The scale marking in the bottom right-hand corner of the micrograph represents 50 µm.
Figure 2B:
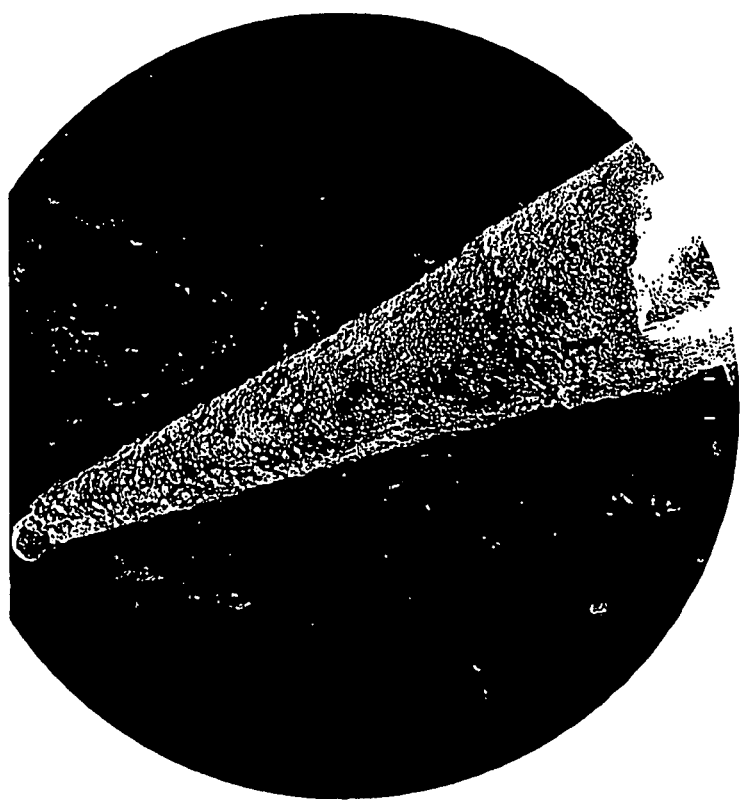
FIG. 2B is a scanning electron micrograph of the microelectrode described for FIG. 2A, showing the rough, platinized tip region of the microelectrode under higher magnification.
Figure 2C:
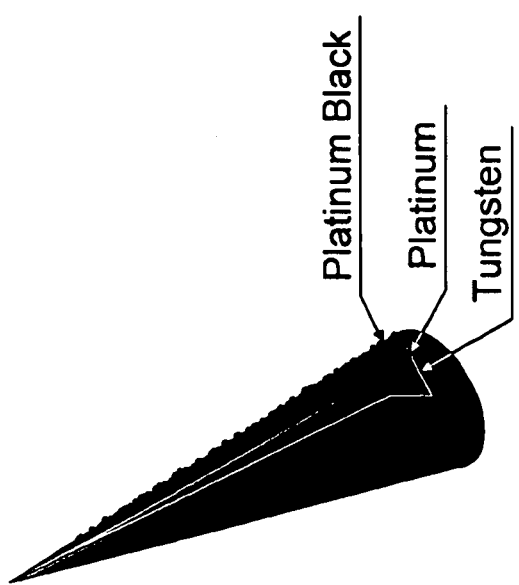
FIG. 2C is a schematic illustration of the tip region of the platinized tungsten-platinum wire microelectrode shown in FIGS. 2A and 2B. The microelectrode comprises an inner tungsten core covered by a layer of platinum. The platinum layer is further coated with a layer of platinum black (i.e., a rough platinum coating).

FIGS. 2A-2C illustrate an example of a single microelectrode that could be covered with a fluorosilane-based xerogel according to the presently disclosed subject matter. More particularly, FIG. 2A shows a micrograph image of a tapered tungsten-platinum wire microelectrode comprising a platinized end. As indicated in FIG. 2A, the diameter of the tapered, rougher, platinized region ranges from about 17 μm where the platinized region joins the smoother, unplatinized region of the microelectrode, to about 5 μm at the tip of the microwire. The length of the platinized region is about 53 μm. FIG. 2B shows the platinized region of the microwire under higher magnification, further illustrating the roughness of the platinum black coating that results from the platinization process. FIG. 2C is a schematic of the platinized region, which shows that the microwire comprises a tungsten (W) core coated with a layer of smooth platinum (Pt). In the platinized region of the microwire electrode, the smooth platinum layer is further coated with a rough layer of platinum (i.e., platinum black). The roughness of the platinum black layer can serve to increase the surface area of the platinized region.

III.A Sensor Formation

In some embodiments, the presently disclosed subject matter provides a method of making a sensor for measuring an amount of a gaseous species in a sample, the method comprising:

(a) providing a silane mixture comprising a fluorosilane and an alkylalkoxysilane;

(b) providing an electrode assembly;

(c) coating at least one portion of the electrode assembly with the silane mixture to form a coated electrode; and (d) drying the coated electrode to form a gas permeable polysiloxane membrane layer on at least one portion of the electrode assembly.

In some embodiments, the silane mixture is dissolved in a solvent. In some embodiments, the solvent comprises an alcohol and water. In some embodiments, the solvent comprises a catalyst, such as a Bronstead acid or base. In some embodiments, the catalyst is hydrochloric acid. Thus, in some embodiments, sol-gel chemistry techniques, such as described hereinabove, provide readily useable methods for macro- and microsensor fabrication, as well as flexibility in optimizing the analytical response characteristics of the sensor.

The electrode assembly can comprise one, two, three, or more electrodes. In some embodiments, the electrode assembly comprises one electrode (i.e., a working electrode). In some embodiments, the sensor includes a two- or a three-electrode configuration. Thus, in some embodiments, the electrode assembly comprises a working electrode and a reference electrode. In some embodiments, the electrode assembly comprises a working electrode, a counter electrode, and a reference electrode. The electrode assembly can further include one or more insulating material or component to physically contain at least a portion of the electrode or electrodes, or to insulate the electrode from one another.

In some embodiments, the electrode assembly is a Clark-type electrode assembly. In some embodiments, the electrode assembly is a single metal wire microelectrode or ultramicroelectrode. In some embodiments, the single metal wire microelectrode or ultramicroelectrode comprises platinized platinum or a platinized platinum/tungsten wire.

During the drying process, the solvent can be evaporated. Some drying conditions can also be used to reduce the porosity of the membrane by leading to additional condensation of any remaining alkoxy and/or hydroxy groups in the network. Thus, in addition to varying the composition of the polysiloxane (e.g., ratio or the chemical composition of the alkylalkoxysilane and the fluorosilane), the method of drying the coated electrode assembly (e.g., the curing conditions) can be used to optimize the sensitivity and selectivity of the sensor.

In some embodiments, the coated electrode assembly can be dried by exposure to ambient conditions for a period of time. Drying under ambient conditions can be referred to as aging. Ambient conditions include exposure to air or dry air (i.e., desiccated air) at room temperature (i.e., between about 20° C. and 25° C.) at atmospheric pressure. The coated electrode assembly can be aged for time periods ranging from several minutes (i.e., 5 min), to one or more hours, or to one to more days.

In some embodiments, the coated electrode assembly can be cured by drying at an increased temperature (i.e., by annealing). For example, the coated electrode assembly can be cured at about 80° C. for a period to time, such as several minutes to several hours.

Further, in some embodiments, the coated electrode assembly can be cured by exposure to a gas at a given pressure. For example, the coated electrode assembly can be cured by exposure to a gas, such as NO or argon gas, at a pressure between about 1 atm and about 5 atm for a period of time.

The curing or drying step of the presently disclosed methods can include any combination of aging, annealing, or exposure to gas at a pressure.

The silane mixture can be coated onto the electrode assembly by any convenient method. For example, an aliquot of the silane mixture can be placed onto a portion of the electrode assembly using a pipette, micropipette, syringe, or microsyringe. Alternatively, the electrode assembly can be dipped into the silane mixture or into a solution comprising the silane mixture. The coating can be done manually or using a robotic or otherwise mechanized device. The portion of the electrode assembly coated will, in general, include at least a portion of the working electrode.

The electrode assembly can be coated with as little as 0.02 μL/mm$^2$ of the silane coating mixture. In some embodiments, the membrane has a thickness of between about 0.1 μm and about 10 μm.

In some embodiments, the thickness of the membrane layer can be optimized for desired permeability or selectivity characteristics. Thus, in some embodiments, the coating or the coating and drying steps can be repeated one or more times to achieve a thicker membrane layer.

In some embodiments, the electrode assembly is coated with an internal electrolyte layer prior to being coated with the silane mixture. In some embodiments, the electrolyte layer is a hydrogel composition, such as, for example, poly(vinylpyrrolidone). A hydrogel internal electrolyte layer can be formed by treating the electrode assembly with a mixture comprising 30 mM sodium chloride, 0.3 mM hydrochloric acid, and 1% poly(vinylpyrrolidone) in water (pH=3.5). For example, the electrode assembly can be dipped into the poly(vinylpyrrolidone) mixture and dried under ambient conditions for 10 min prior to coating with the silane mixture. The thickness of such an internal electrolyte layer can be, for example, approximately 1.5 μM.

III.B. Sensor Uses

In some embodiments, the presently disclosed subject matter provides a method of measuring the amount of a gaseous species in a sample. The sample can be a biological sample or an environmental sample. In particular, the presently disclosed sensors can be used to specifically and quantitatively detect a gaseous species that is dissolved in a solution, such as an aqueous solution of biological media, either in vitro or in vivo. Thus, in some embodiments, the sensor is a biosensor. In some embodiments, the gas is oxygen or nitric oxide. In particular embodiments, sensors provided by the presently disclosed subject matter can detect nitric oxide.

In some embodiments, the sensors can detect and quantify nitric oxide or another gaseous species present in a sample at low levels, for example, at levels as low as about 10 nM. In some embodiments, the gaseous species is present at a concentration as low as about 200 pM. For example, the sensors can selectively measure a gaseous species at concentration levels between about 200 pM and about 4 μM. In some embodiments, the gaseous species is at a concentration of between about 200 pM and about 300 nM. In some embodiments, the gaseous species is at a concentration of between about 200 pM and about 3 nM.

Thus, the presently disclosed sensors include nitric oxide sensors that can be used as research tools to investigate the biological actions of NO, to monitor medical conditions related to NO-regulated processes, and to monitor the degradation, therapeutic, or adverse actions of a variety of therapeutics, including the actions of NO-releasing therapeutics, such as nitroglycerin or amyl nitrite. NO-releasing therapeutics include those which release NO themselves, as well as those which trigger the release of NO by the body. In some embodiments, the presently disclosed sensors can be used as neurochemical research or medical diagnostic tools.

In some embodiments, the biological sample in which the gas is being measured is one of a cell, a tissue, an organ, or a biological fluid. Cells can include, for example, heart cells, brain cells, macrophage cells, neutrophil cells, monocyte cells, and endothelial cells. Biological fluids can include blood, plasma, gastric fluid, milk, saliva, cerebrospinal fluid (CSF) and the like. Biological samples can also include cell cultures, tissue cultures and cell or tissue extracts.

In some embodiments, the sensors can be used to measure NO in the brain or in a brain cell or brain tissue. In some embodiments, the sensors can be used to measure NO levels in blood, for example in a blood vessel. In some embodiments, the sensors can be used to determine an immune response by measuring NO in a macrophage cell, a neutrophil cell, or in tissue comprising or believed to comprise a macrophage and/or neutrophil cell. In some embodiments, the sensors can be used to measure the NO concentration in a single cell.

In some embodiments, the methods of the presently disclosed subject matter can be useful for measuring the concentration of nitric oxide (or another biologically relevant gaseous species) in a biological sample derived from or present in a subject. In some embodiments, the subject is a human subject, although it is to be understood that the subject can be any living organism, including microbes, plants, and animals.

Accordingly, the term "subject" as used herein, refers to any invertebrate or vertebrate species. The methods and sensors of the presently disclosed subject matter are particularly useful as diagnostic and research tools for use with samples from warm-blooded vertebrates. Thus, the presently disclosed subject matter concerns mammals and birds. More particularly, herein provided are methods for the study and/or diagnosis of mammals, such as humans, as well as those mammals of importance due to being endangered (such as Siberian tigers), of economical importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), and horses. Also provided is the study and diagnosis of birds, including those kinds of birds that are endangered, kept in zoos, as well as fowl, and more particularly domesticated fowl, e.g., poultry, such as turkeys, chickens, ducks, geese, guinea fowl, and the like, as they also are of economical importance to humans. Thus, subjects include livestock, including, but not limited to, domesticated swine (pigs and hogs), ruminants, horses, poultry, and the like. Subjects also include animals generally used in biological or medical research, such as rodents (e.g., rats, mice and hamsters) and primates.

In some embodiments, the sample is derived from, but is no longer present in a living subject. Thus, in some embodiments, NO can be measured in a sample ex vivo. In some embodiments, the sample is present in a living subject, and NO concentration can be measured in a sample in vivo. In some embodiments, the sample is an environmental sample, such as an air sample or a water sample taken from, for example, a lake, a river, a stream, a pond, or any other outdoor water source. Thus, for example, the presently disclosed sensors can be used to measure NO levels in air, produced, for example, as waste from combustion engines or power plants. The sensors can also be used to quantitate levels of dissolved NO or $O_2$ in aquatic environments, to assess the ability of such environments to sustain animal or plant life.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

Preparation and characterization of the presently disclosed networks, membranes, and sensors can be performed analogously to methods described previously. See, for example, Shin, J. H., et al., *Anal. Chem.*, 77, 3494-3501 (2005), which is incorporated herein by reference in its entirety. Silanes were obtained from Aldrich (Milwaukee, Wis., United States of America) or Gelest (Tullytown, Pa., United States of America).

Example 1

Permeability and Selectivity of Fluorosilane-Based Xerogels

Xerogel casting solutions were prepared by mixing 40 μL of MTMOS (Aldrich, Milwaukee, Wis., United States of America) and 10 μL of fluorosilane (either (3,3,3-trifluoropropyl)trimethoxysilane (3FTMS), nonafluorohexyltrimethoxysilane (9FTMS), (tridecafluoro-1,1,2,2-tetrahydrooctyl)-trimethoxysilane (13FTMS) or (heptadecafluoro-1,1,2,2-tetrahydrodecyl)trimethoxysilane (17FTMS)) with 200 μL ethanol (EtOH) and 100 μL water for 10 min. The synthesis of the xerogel was catalyzed by the addition of 10 μL of 0.5 M HCl. The solution was then deposited onto a platinized platinum working macroelectrode (platinized with a platinizing solution of 3% chloroplatinic acid and 0.1% lead acetate in water).

The permeability of the cured xerogels to NO and nitrite ($NO_2^-$) were evaluated electrochemically according to previously described procedures by measuring the ratio of peak currents at the xerogel-coated and bare Pt electrodes in 10 μM NO and 100 μM nitrite solutions. See Shin, J. H., et al., *Anal. Chem.*, 77, 3494-3501 (2005). The selectivity of the xerogel-modified sensors for NO in the presence of nitrite was determined using the separation solution method, also according to previously described procedures. See Shin, J. H., et al., *Anal. Chem.*, 77, 3494-3501 (2005).

Figure 3:
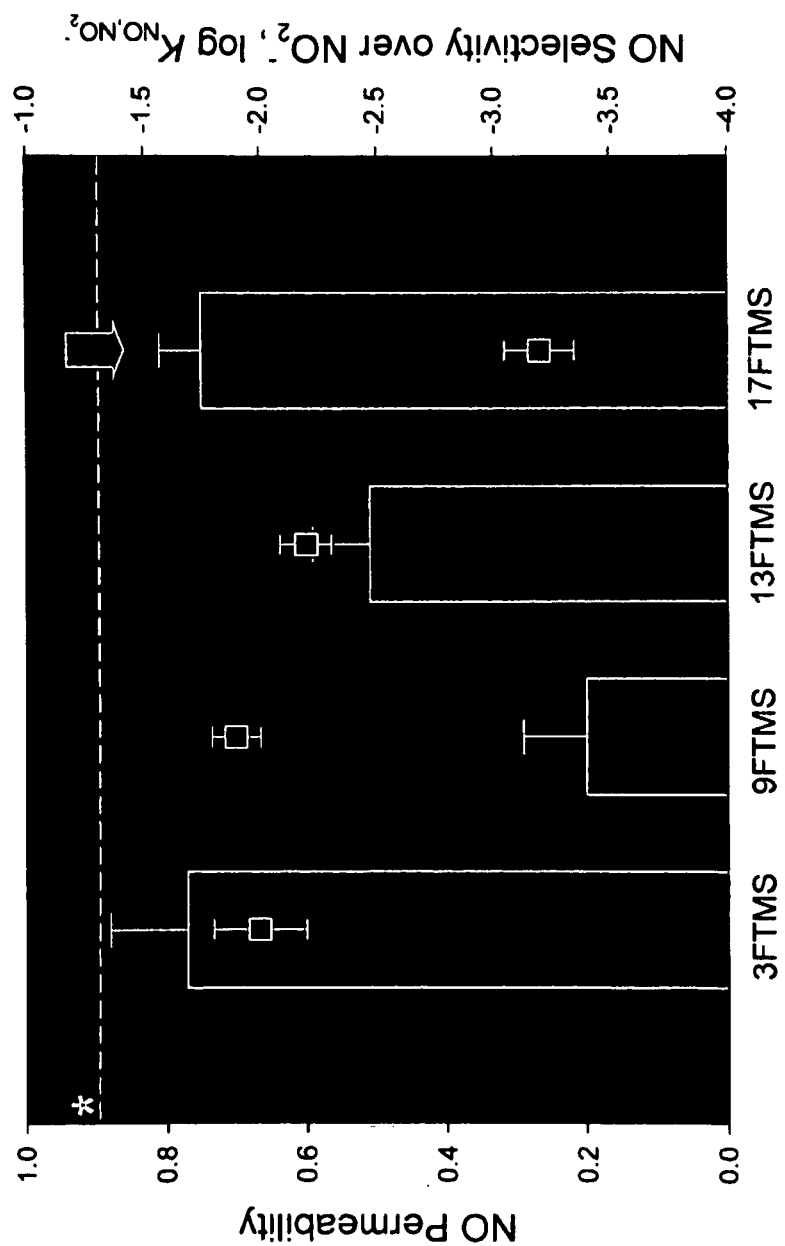
FIG. 3 is a composite graph showing the nitric oxide (NO) permeability (bar graph, for left axis) and selectivity over nitrite ($NO_2^-$) (scatter plots, for right axis) of xerogel membranes of varying chemical composition coated on platinum macroelectrodes. The xerogel membranes were prepared from a mixture of 80% by volume methyltrimethoxysilane (MTMOS) and 20% by volume fluorosilane (i.e., (3,3,3-trifluoropropyl)trimethoxysilane (3FTMS), nonafluorohexyltrimethoxysilane (9FTMS), (tridecafluoro-1,1,2,2-tetrahydrooctyl)-trimethoxysilane (13FTMS) or (heptadecafluoro-1,1,2,2-tetrahydrodecyl)trimethoxysilane (17FTMS)). The dashed line indicates nitric oxide over nitrite selectivity of the bare Pt electrode.

The results of the permeability and selectivity testing are shown in FIG. 3. As indicated by the bar (medium gray) graph portion of FIG. 3, the xerogels comprising 3FTMS and 17FTMS had the highest NO permeability. As indicated by the scatter graph (light colored squares) portion of FIG. 3, xerogels comprising 17FTMS were most effective at discriminating NO over $NO_2^-$ under the noted conditions.

Example 2

Fluorosilane-Based Xerogel Membrane Microsensor

A casting solution was prepared by mixing 40 μL of MTMOS (Aldrich, Milwaukee, Wis., United States of America) and 10 μL (Heptadeca-fluoro-1,1,2,2-tetrahydrodecyl)triethoxysilane (Gelest, Tullytown, Pa., United States of America) with 200 μL ethanol (EtOH) and 100 μL water for 10 min. The synthesis of the xerogel was catalyzed by the addition of 10 μL of 0.5 M HCl. The solution was then deposited onto a platinized platinum working microelectrode (platinized with a platinizing solution of 3% chloroplatinic acid and 0.1% lead acetate in water).

After curing, NO response and calibration curves for the xerogel-modified microelectrode were obtained by injecting aliquots of a standard NO solution (1.9 mM) into 100 mL phosphate buffered saline (PBS, pH 7.4) at room temperature under constant stirring. Amperometric measurements were performed using a CH Instruments 660A potentiostat (CH Instruments, Inc., Austin, Tex., United States of America). Currents were recorded at an applied potential of +0.8 V (vs an Ag/AgCl reference electrode). The xerogel-modified microelectrode was prepolarized for at least 30 min prior to use.

Figure 4:
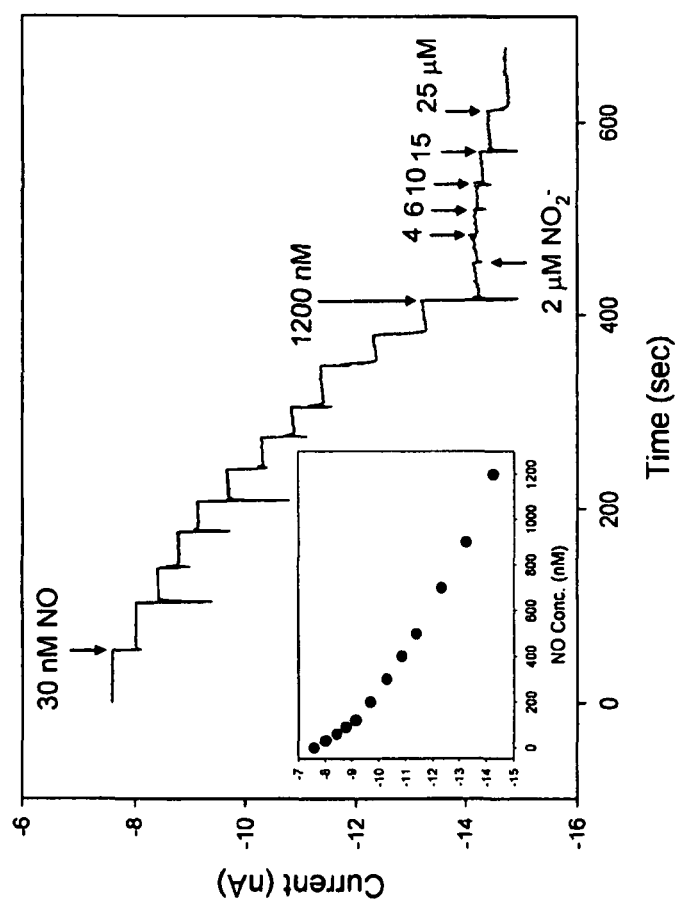
FIG. 4 is a composite graph of the dynamic response and calibration (inset) curves of a platinized platinum (Pt) microelectrode coated with a membrane comprising a co-condensed network of a silane mixture comprising 20% by volume (heptadecafluoro-1,1,2,2-tetrahydrodecyl) triethoxysilane (remainder methyltrimethoxysilane, (MTMOS)). The curves show the response of the coated microelectrode to nitric oxide at concentrations between 30 nM and 1200 nM (as indicated by the captions and arrows). The right-hand side of the dynamic response curve also shows the response of the coated microelectrode to nitrite ($NO_2^-$) at concentrations between 2 µM and 25 µM (also as indicated by the captions and arrows).

FIG. 4 shows the response and calibration curve (inset) for the modified microelectrode over an NO concentration range of 30 nM to 1200 nM. Each drop in the dynamic response curve indicates the addition of an aliquot of the NO solution. The response of the modified microelectrode was also assayed for the potentially interfering molecular species, nitrite ($NO_2^-$). As shown in the dynamic response curve, after about 450 sec, aliquots of a solution of nitrite were added to the PBS solution, to determine the response of the modified microelectrode to nitrite at concentrations between 2 μM and 25 μM. The nitrite solution was prepared from sodium nitrite (Sigma Chemical Co., St. Louis, Mo., United States of America). As indicated in FIG. 4 (and as expected based on the data described in Example 1), the coated microelectrode appeared to be significantly less sensitive to nitrite than to NO.

Figure 5:
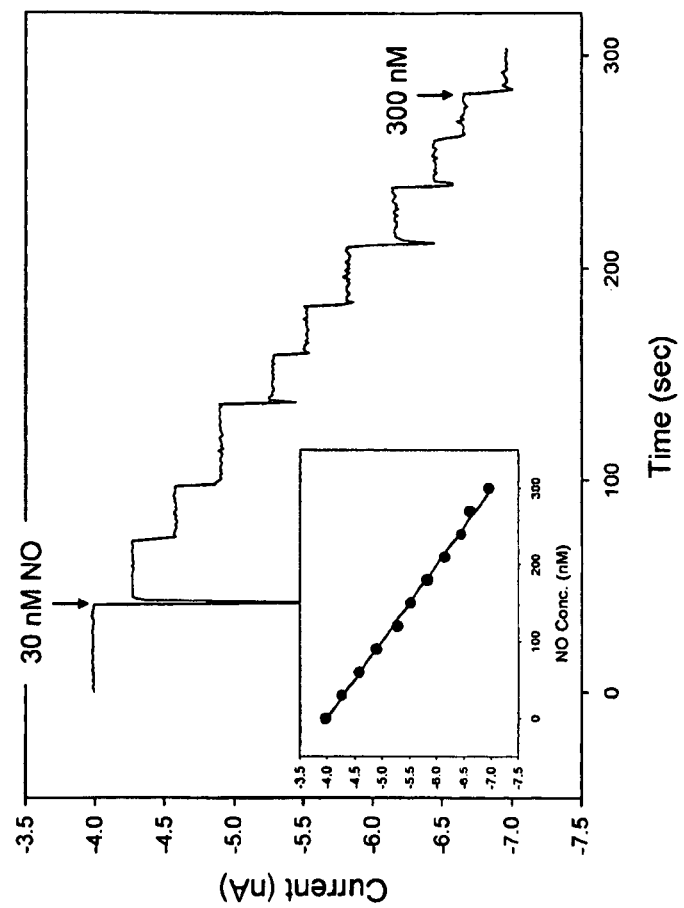
FIG. 5 is a composite graph showing expansions of the dynamic response and calibration (inset) curves shown in FIG. 4 at nitric oxide concentrations between 30 nM and 300 nM. The slope of the calibration curve is −9.96 pA/nM; linearity (r)=0.9987.

FIG. 5 shows an expansion of the response curve and calibration curve (inset) from FIG. 4 at NO concentrations between 30 nM and 300 nM. The calibration curve shows that the coated microelectrode has a linear response to NO concentrations between 30 nM and 300 nM (slope of −9.96 pA/nM; r=0.9987). The slope of the calibration curve corresponds to the response sensitivity of the coated microelectrode.

Figure 6A:
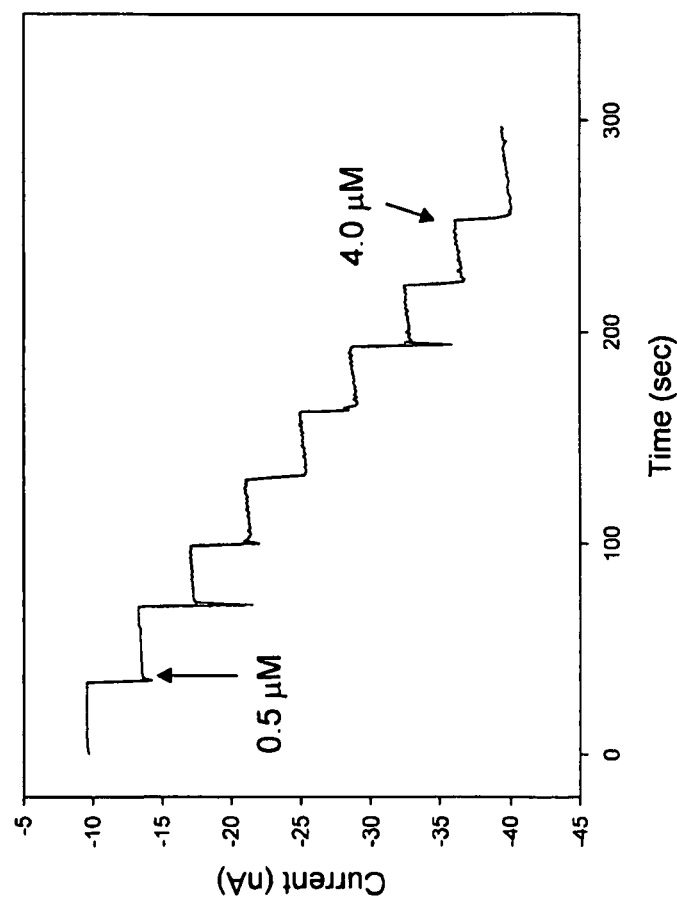
FIG. 6A is the dynamic response curve of the coated microelectrode described in FIG. 4 at nitric oxide concentrations between 0.5 µM and 4.0 µM.
Figure 6B:
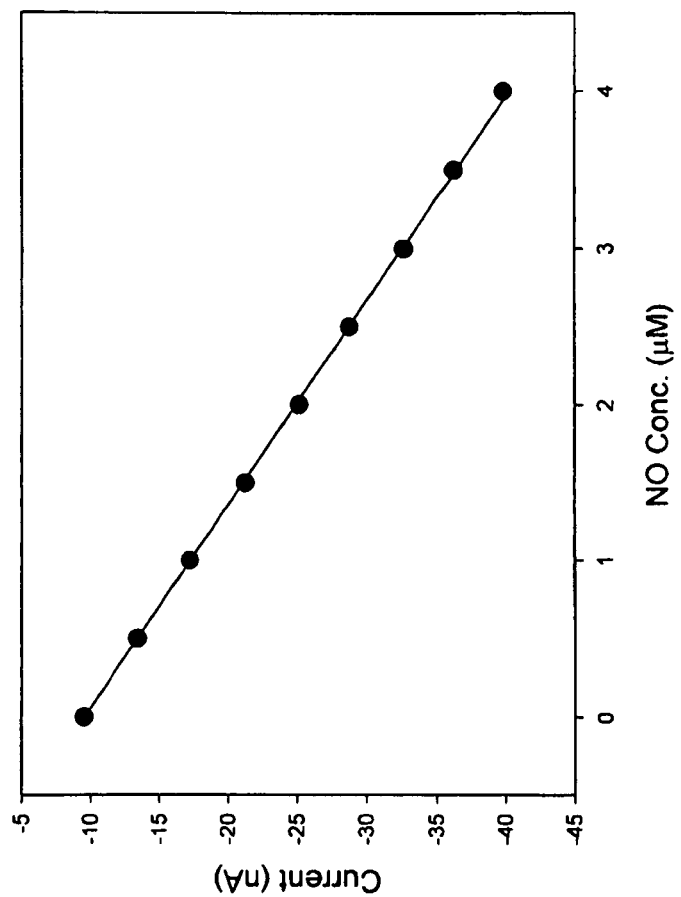
FIG. 6B is the calibration curve corresponding to the dynamic response curve shown in FIG. 6A. The slope is −7.60 nA/µM; the linearity (r)=0.9999.
Figure 7A:
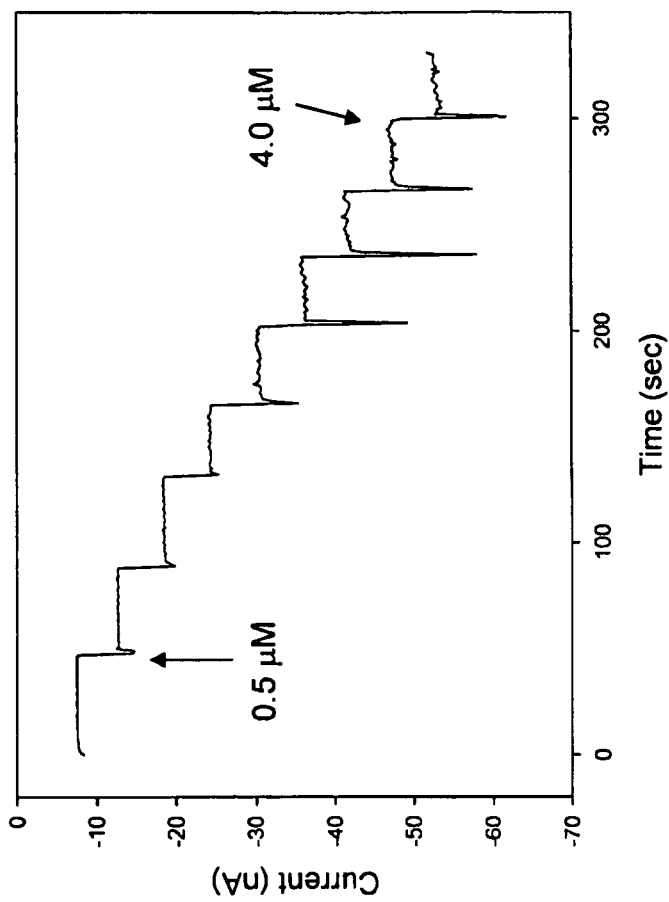
FIG. 7A is a dynamic response curve of a non-coated platinized platinum microelectrode at nitric oxide concentrations between 0.5 µM and 4.0 µM.
Figure 7B:
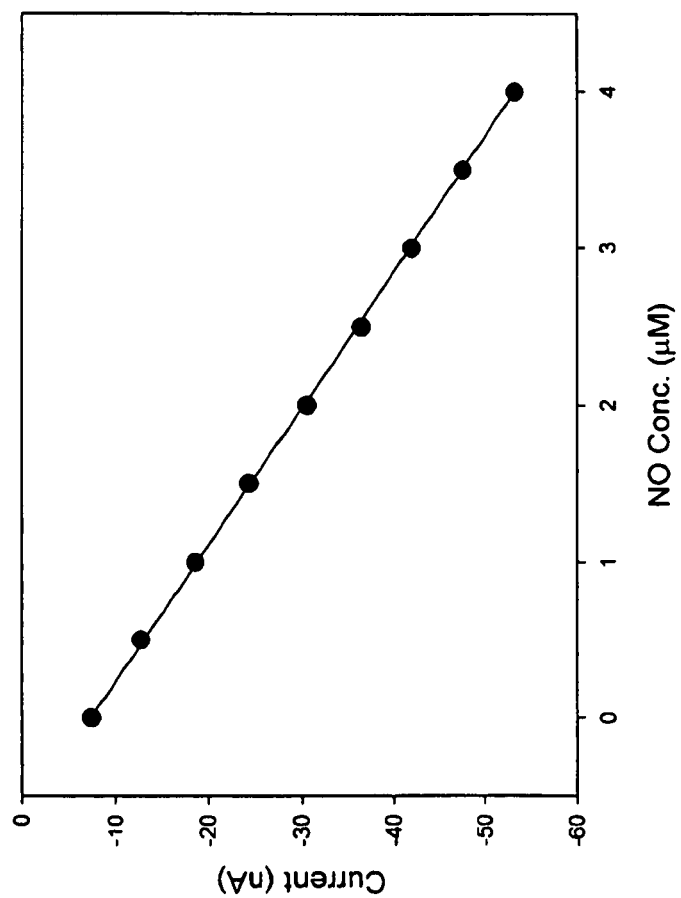
FIG. 7B is the calibration curve corresponding to the dynamic response curve shown in FIG. 7A. The slope is −11.57 nA/µM, the linearity is 0.9999.

FIG. 6A shows the dynamic response curve for the coated microelectrode to NO concentrations between 0.5 μM and 4.0 μM. The slope of the corresponding calibration curve (shown in FIG. 6B) is −7.60 nA/mM (r=0.9999). In comparison, the dynamic response curve and calibration curve of a non-coated microelectrode (i.e., a bare platinized platinum electrode) to NO in the same concentration range are shown in FIGS. 7A and 7B. The slope of the calibration curve of the bare platinized platinum electrode is −11.57 nA/mM (r=9999).

Figure 8:
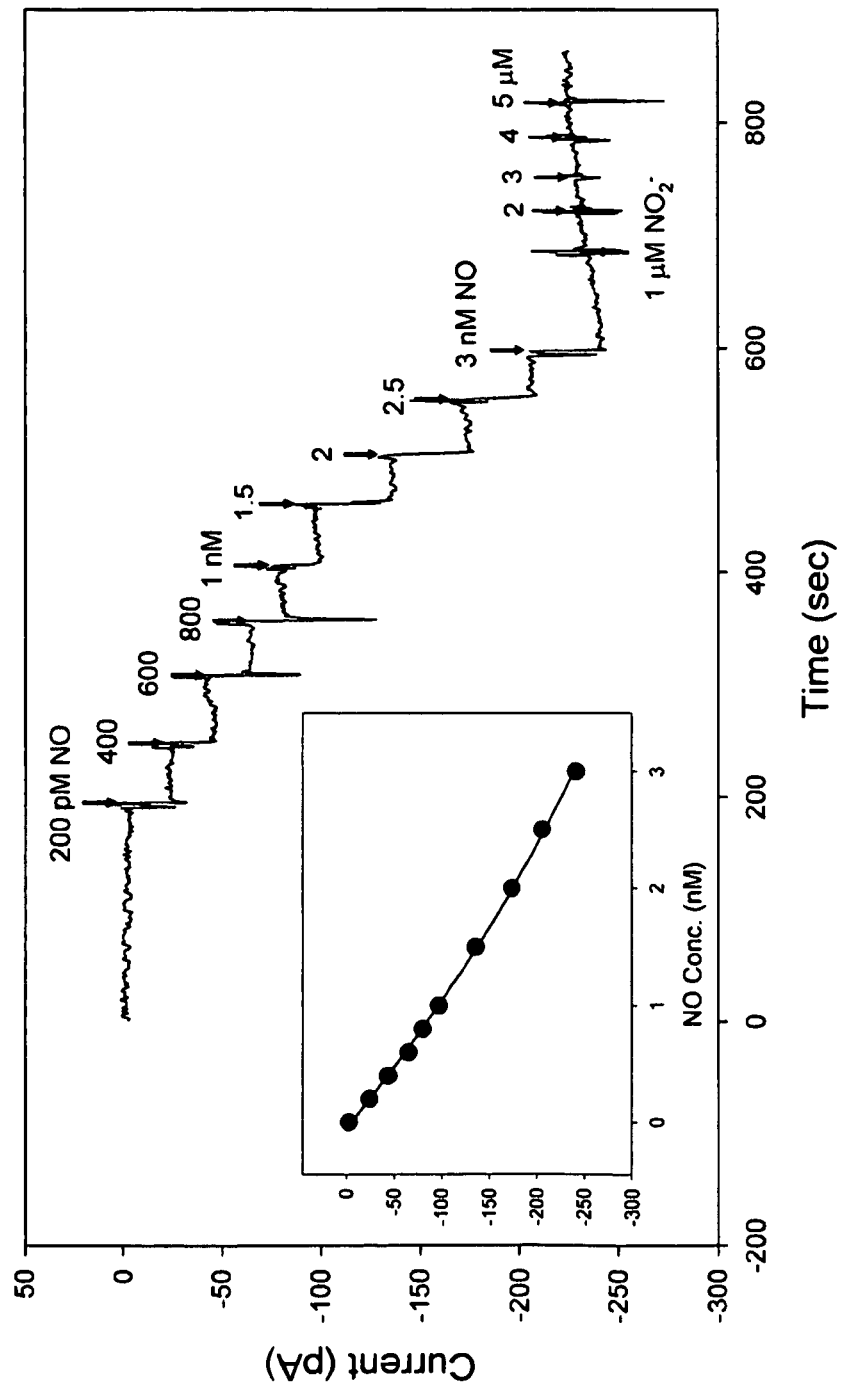
FIG. 8 is a composite graph of the dynamic response and calibration (inset) curves of the coated microelectrode described in FIG. 4 at nitric oxide concentrations between 200 pM and 3 nM (as indicated by the captions and arrows). The right-hand side of the dynamic response curve also shows the response of the coated microelectrode to nitrite ($NO_2^-$) at concentrations between 1 µM and 5 µM (also as indicated by the captions and arrows).

FIG. 8 shows the dynamic response curve and calibration curve (inset) for the coated microelectrode at nitric oxide concentrations between 200 pM and 3 nM. The right-hand side of the dynamic response curve also shows the response of the coated microelectrode to $NO_2^-$ at concentrations between 1 μM and 5 μM.

Example 3

Oxygen Response of Fluorosilane-Based Xerogel-Coated Sensors

A membrane-coated macroelectrode sensor was prepared using a membrane casting solution comprising 20% by volume (heptadecafluoro-1,1,2,2-tetrahydrodecyl)triethoxysilane and 80% by volume methyltrimethoxysilane (MTMOS). The casting solution was prepared as described in Example 2, above. The sensor comprised a three-electrode assembly configuration having a Pt working electrode (2 mm), a Pt wire counter electrode (0.6 mm) and an Ag/AgCl (3.0 M KCl) reference electrode.

Oxygen response and calibration curves were obtained using previously described methods. See Marxer, S. M., et al., Analyst, 130, 206-212 (2005). More particularly, the membrane-coated electrode assembly was placed into phosphate-buffered saline (PBS) solutions saturated with 0, 36, 72, 151, or 360 mmHg $O_2$. The PBS solutions were at room temperature and were constantly stirred. Amperometric measurements were performed using a CH Instruments 660A potentiostat (CH Instruments, Inc., Austin, Tex., United States of America). Currents were recorded at an applied potential of −0.65 V (vs an Ag/AgCl reference electrode).

Figure 9:
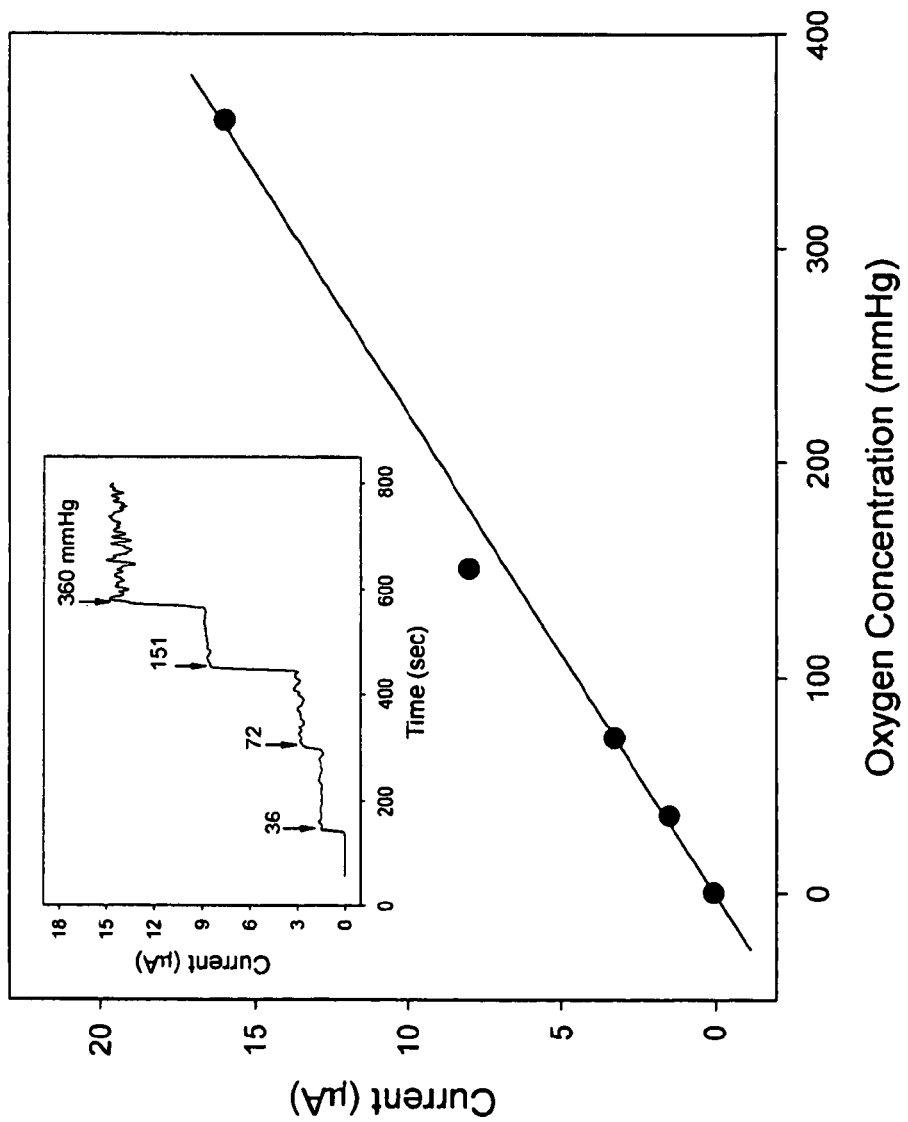
FIG. 9 is a composite graph of the dynamic response (inset) and calibration curves of a macroelectrode coated with a membrane comprising a co-condensed network of a silane mixture comprising 20% by volume (heptadecafluoro-1,1,2, 2-tetrahydrodecyl)triethoxysilane (remainder (i.e., 80% by volume) methyltrimethoxysilane, (MTMOS)). The calibration curve shows that the coated macroelectrode has a linear response to oxygen gas ($O_2$) at concentrations between 36 and 360 mmHg (slope=44.7 nA/mmHg; r=0.9908). The dynamic response curve also shows the response of the coated macroelectrode to $O_2$ at concentrations of 36, 72, 151, and 360 mmHg (as indicated by the captions and arrows).

Oxygen response and calibration curves are shown in FIG. 9. As indicated by the calibration curve, the membrane-coated macroelectrode had a linear response to $O_2$ at concentrations between 36 mmHg and 360 mmHg.

Example 4

Biocompatibility of Fluorosilane-Based Xerogel Membranes

The biocompatibility of the presently disclosed fluorosilane-based xerogel membranes was determined by assessing the membranes' ability to resist platelet adhesion. Platelet adhesion resistance was determined according to previously disclosed methods. See Marxer, S. M., et al., Analyst, 130, 206-212 (2005).

More particularly, acid citrate dextrose (ACD)-anticoagulated porcine blood (3 parts ACD to 20 parts whole blood) was centrifuged at 200×g for 30 min at room temperature to obtain platelet rich plasma (PRP). Calcium chloride was added to the PRP to a final concentration of 0.25-0.50 mM $Ca^{2+}$ to maintain normal platelet activity. Fluorosilane-based xerogel membrane-coated glass slides were immersed in the PRP for 1 hour at 37° C. in a humid environment. The slides were rinsed with Tyrode's buffer (pH 7.4) to remove loosely adhered platelets. The attached platelets were then fixed with a 1% glutaraldehyde solution (v/v, Tyrode's buffer) for 30 min. The slides were rinsed with Tyrode's buffer and water and chemically dried by immersion in 50%, 75%, and 95% ethanol (v/v, water) for 5 min each, followed by immersion in 100% ethanol for 10 minutes and finally in hexamethyldisilazane for about 12 hours.

Figure 10:
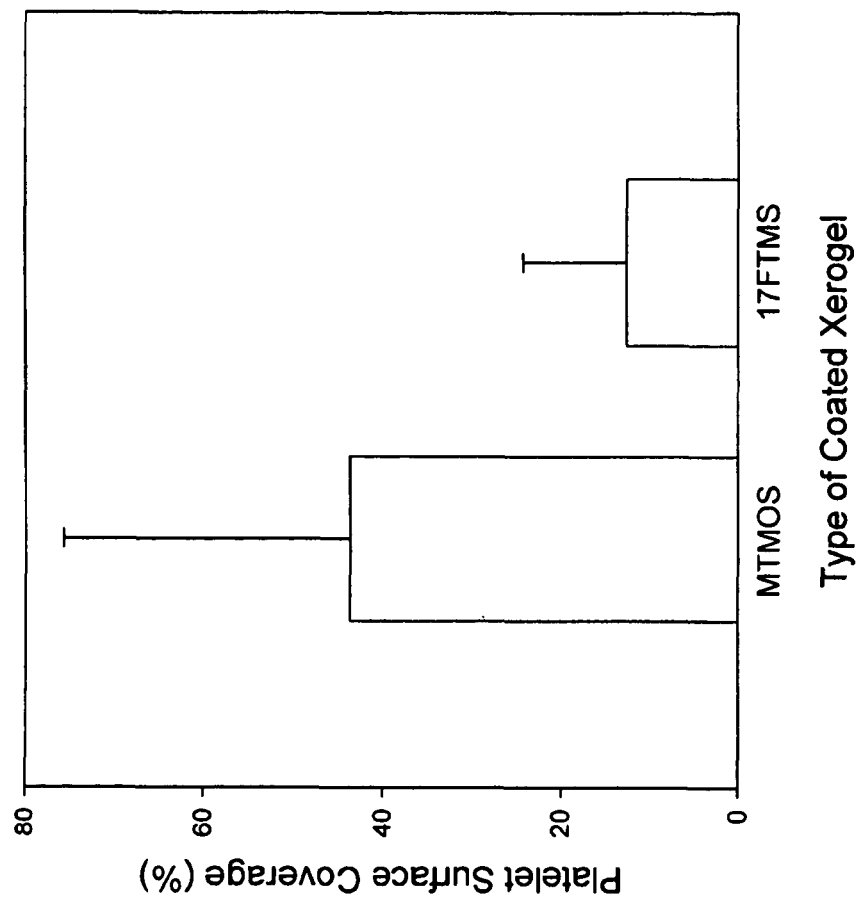
FIG. 10 is a bar graph showing porcine platelet adhesion to xerogel-coated glass slides. The bar indicated by 17FTMOS refers to a glass slide coated with a xerogel comprising a co-condensed network of a silane mixture comprising 20% by volume (heptadecafluoro-1,1,2,2-tetrahydrodecyl)triethoxysilane (remainder (i.e., 80% by volume) methyltrimethoxysilane (MTMOS)). The bar indicated by MTMOS refers to a glass slide coated with a xerogel prepared by the condensation of MTMOS. Values were determined relative to platelet adhesion observed for an uncoated glass slide.

Phase contrast images of the slides were obtained using a Zeiss Axiovert 200 inverted microscope (Carl Zeiss Micro-Imaging, Inc., Chester, Va., United States of America). The amount of platelet adhesion on the xerogel membrane-coated slides was compared relative to that of non-coated glass slides. The relative platelet adhesion of a fluorosilane-based xerogel membrane-coated glass slide prepared from a casting solution comprising a silane mixture of 20% by volume (heptadecafluoro-1,1,2,2-tetrahydrodecyl)triethoxysilane and 80% by volume MTMOS is shown in FIG. 10 (right-hand bar, indicated by 17FTMS). Relative platelet adhesion to a xerogel membrane-coated glass slide prepared from a casting solution comprising a single silane, MTMOS, is also shown in FIG. 10 (left-hand bar, indicated by MTMOS).

REFERENCES

The references listed below as well as all references cited in the specification are incorporated herein by reference to the extent that they supplement, explain, provide a background for or teach methodology, techniques and/or compositions employed herein. All cited patents and publications referred to in this application are herein expressly incorporated by reference.

Marxer, S. M., et al., Analyst, 130, 206-212 (2005).
Shin, J. H., et al., Anal. Chem., 77, 3494-3501 (2005).
Zhang, X., Frontiers in Bioscience, 9, 3434-3446 (2004).

It will be understood that various details of the presently disclosed subject matter can be changed without departing from the scope of the presently disclosed subject matter. Furthermore, the foregoing description is for the purpose of illustration only, and not for the purpose of limitation.

What is claimed is:

1. A method of measuring an amount of a gaseous species in a sample, the method comprising contacting the sample with a sensor comprising a polysiloxane membrane; wherein:
the polysiloxane membrane comprises one or more silicon atoms covalently attached to an alkyl group and one or more silicon atoms covalently attached to a fluorinated alkyl group, wherein the polysiloxane membrane is a condensation product of a silane mixture comprising an alkyl alkoxysilane and a fluorosilane,
wherein the fluorosilane comprises a structure having a formula:

wherein:
m is 0 to 15;
n is 1 to 5;
p is 1, 2, or 3;
each X is independently selected from the group consisting of alkoxy, aryloxy, aralkoxy, hydroxyl, and halo; and
each Y is independently selected from the group consisting of H, alkyl, aryl, and aralkyl; and the polysiloxane membrane selectively allows the gaseous species in the sample to be measured by the sensor.

2. The method of claim 1, wherein the sensor is an amperometric sensor.

3. The method of claim 2, wherein the polysiloxane membrane is positioned between the sample and an electrode assembly.

4. The method of claim 3, wherein the electrode assembly is selected from the group consisting of:
a electrode assembly comprising a working electrode;
an electrode assembly comprising a working electrode and a reference electrode;
and an electrode assembly comprising a working electrode, a reference electrode, and a counter electrode.

5. The method of claim 1, wherein the sample is a biological sample or an environmental sample.

6. The method of claim 5, wherein the sample is a biological sample selected from the group consisting of a cell, a tissue, a biological fluid, and extracts thereof.

7. The method of claim 6, wherein the sample is selected from brain tissue, a brain cell, or blood.

8. The method of claim 6, wherein the sample is in a living subject.

9. The method of claim 8, wherein the sample is in the brain of a living subject.

10. The method of claim 1, wherein the gaseous species is selected from the group consisting of nitric oxide and oxygen.

11. The method of claim 1, wherein the gaseous species is present in the sample at a concentration as low as about 200 pM.

12. A sensor for measuring an amount of a gaseous species in a sample, the sensor comprising:
(a) an electrode assembly;
(b) a gas permeable membrane located between one or more surfaces of the electrode assembly and the sample, wherein the membrane comprises a polysiloxane network wherein one or more silicon atoms in the polysiloxane network is covalently attached to an alkyl group and one or more silicon atoms in the polysiloxane network is covalently attached to a fluorinated alkyl group, wherein the polysiloxane network is a condensation product of a silane mixture comprising an alkylalkoxysilane and a fluorosilane;
wherein the fluorosilane comprises a structure having a formula:

wherein:
m is 0 to 15;
n is 1 to 5;
p is 1, 2, or 3;
each X is independently selected from the group consisting of alkoxy, aryloxy, aralkoxy, hydroxyl, and halo; and
each Y is independently selected from the group consisting of H, alkyl, aryl, and aralkyl;
and
(c) a detector for measuring current at the electrode assembly.

13. The sensor of claim 12, wherein the gaseous species is selected from nitric oxide and oxygen.

14. The sensor of claim 12, wherein the electrode assembly is selected from the group consisting of:
an electrode assembly comprising a working electrode;
an electrode assembly comprising a working electrode and a reference electrode; and an electrode assembly comprising a working electrode, a reference electrode, and a counter electrode.

15. The sensor of claim 14, wherein the working electrode is selected from platinum, platinized platinum, tungsten, gold, carbon, carbon fiber, and combinations thereof.

16. The sensor of claim 14, wherein the reference electrode comprises silver/silver chloride.

17. The sensor of claim 14, wherein the counter electrode comprises platinum.

18. The sensor of claim 12, wherein the fluorosilane is selected from the group consisting of:
(3,3,3-trifluoropropyl)trimethoxysilane;
nonafluorohexyltrimethyoxysilane;
nonafluorohexyltriethoxysilane;
(tridecafluoro-1,1,2,2-tetrahydrooctyl)trimethoxysilane;
(tridecafluoro-1,1,2,2-tetrahydrooctyl)triethoxysilane;
(tridecafluoro-1,1,2,2-tetrahydrooctyl)trichlorosilane;
(heptadecafluoro-1,1,2,2-tetrahydrodecyl)trimethoxysilane;
(heptadecafluoro-1,1,2,2-tetrahydrodecyl)triethoxysilane;
(perfluoroalkyl)ethyltriethoxysilane;
(heptadecafluoro-1,1,2,2-tetrahydrodecyl)trichlorosilane;
and combinations thereof.

19. The sensor of claim 12, wherein the alkylalkoxysilane is selected from the group consisting of:
methyltrimethoxysilane (MTMOS);
ethyltrimethoxysilane;
propyltrimethoxysilane;
butyltrimethoxysilane (BTMOS);
hexyltrimethoxysilane (HTMOS);
octyltrimethoxysilane (OTMOS); and
combinations thereof.

20. The sensor of claim 12, wherein the silane mixture comprises about 1% to about 99% by volume fluorosilane.

21. The sensor of claim 20, wherein the silane mixture comprises about 5% to about 50% by volume fluorosilane.

22. The sensor of claim 21, wherein the silane mixture comprises about 20% by volume fluorosilane.

23. The sensor of claim 22, wherein the silane mixture comprises about 20% by volume (heptadecafluoro-1,1,2,2-tetrahydrodecyl)triethoxy-silane and about 80% by volume methyltrimethoxysilane.

24. The sensor of claim 12, wherein the sensor further comprises an internal electrolyte layer, wherein the internal electrolyte layer is located between the electrode assembly and the gas permeable membrane.

25. The sensor of claim 24, wherein the internal electrolyte layer is a hydrogel composition.

26. The sensor of claim 25, wherein the hydrogel composition comprises poly(vinylpyrrolidone).

27. A method of making a sensor for measuring an amount of a gaseous species in a sample, the method comprising:
(a) providing a silane mixture comprising a fluorosilane and an alkylalkoxysilane,
wherein the fluorosilane comprises a structure having a formula:
$F_3C-(CF_2)_m-(CH_2)_n-Si(X)_p(Y)_{3-p}$
wherein:
m is 0 to 15;
n is 1 to 5;
p is 1, 2, or 3;
each X is independently selected from the group consisting of alkoxy, aryloxy, aralkoxy, hydroxyl, and halo; and
each Y is independently selected from the group consisting of $H_1$ alkyl, aryl, and aralkyl;
(b) providing an electrode assembly;
(c) coating at least one portion of the electrode assembly with the silane mixture to form a coated electrode; and
(d) drying the coated electrode to form a gas permeable polysiloxane membrane layer on at least one portion of the electrode assembly.

28. The method of claim 27, wherein the fluorosilane is selected from the group consisting of:
(3,3,3-thfluoropropyl)trimethoxysilane;
nonafluorohexyltrimethyoxysilane;
nonafluorohexyltriethoxysilane;
(tridecafluoro-1,1,2,2-tetrahydrooctyl)trimethoxysilane;
(tridecafluoro-1,1,2,2-tetrahydrooctyl)triethoxysilane;
(tridecafluoro-1,1,2,2-tetrahydrooctyl)trichlorosilane;
(heptadecafluoro-1,1,2,2-tetrahydrodecyl)trimethoxysilane;
(heptadecafluoro-1,1,2,2-tetrahydrodecyl)triethoxysilane;
(perfluoroalkyl)ethyltriethoxysilane;
(heptadecafluoro-1,1,2,2-tetrahydrodecyl)trichlorosilane;
and combinations thereof.

29. The method of claim 27, wherein the alkylalkoxysilane is selected from the group consisting of:
methyltrimethoxysilane (MTMOS);
ethyltrimethoxysilane;
propyltrimethoxysilane;
butyltrimethoxysilane (BTMOS);
hexyltrimethoxysilane (HTMOS);
octyltrimethoxysilane (OTMOS); and combinations thereof.

30. The method of claim 27, wherein the silane mixture comprises about 1% to about 99% by volume fluorosilane.

31. The method of claim 30, wherein the silane mixture comprises about 5% to about 50% by volume fluorosilane.

32. The method of claim 31, wherein the silane mixture comprises about 20% by volume fluorosilane.

33. The method of claim 32, wherein the silane mixture comprises about 20% by volume (heptadecafluoro-1,1,2,2-tetrahydrodecyl)-triethoxysilane and 80% by volume methyltrimethoxysilane.

34. The method of claim 27, wherein the silane mixture is dissolved in a solvent.

35. The method of claim 34, wherein the solvent comprises an alcohol and water.

36. The method of claim 35, wherein the alcohol is ethanol.

37. The method of claim 34, wherein the solvent further comprises a catalyst.

38. The method of claim 37, wherein the catalyst is hydrochloric acid.

39. The method of claim 27, wherein the electrode assembly is selected from the group consisting of:
an electrode assembly comprising a working electrode;
an electrode assembly comprising a working electrode and a reference electrode; and
an electrode assembly comprising a working electrode, a reference electrode, and a counter electrode.

40. The method of claim 39, wherein the working electrode is selected from platinum, platinized platinum, tungsten, gold, carbon, carbon fiber, and combinations thereof.

41. The method of claim 39, wherein the reference electrode comprises silver/silver chloride.

42. The method of claim 39, wherein the counter electrode comprises platinum.

43. The method of claim 27, wherein the drying takes place at ambient temperature.

44. The method of claim 27, wherein the drying takes place at an elevated temperature.

45. The method of claim 27, wherein the drying step comprises exposing the membrane layer to one of nitric oxide or argon at a pressure.

46. The method of claim 27, wherein the coating is performed by dipping the electrode assembly into the silane mixture.

47. The method of claim 27, further comprising repeating the coating and drying steps one or more times to provide a thicker membrane layer.

48. The method of claim 27, wherein prior to coating the at least one portion of the electrode assembly with the silane mixture, the at least one portion of the electrode assembly is coated with a hydrogel material.

* * * * *